US006818418B1

(12) United States Patent
Lipovsek et al.

(10) Patent No.: US 6,818,418 B1
(45) Date of Patent: Nov. 16, 2004

(54) PROTEIN SCAFFOLDS FOR ANTIBODY MIMICS AND OTHER BINDING PROTEINS

(75) Inventors: Dasa Lipovsek, Cambridge, MA (US); Richard W. Wagner, Concord, MA (US); Robert G. Kuimelis, Brighton, MA (US)

(73) Assignee: Compound Therapeutics, Inc., Waltham, MA (US)

( * ) Notice: Subject to any disclaimer, the term of this patent is extended or adjusted under 35 U.S.C. 154(b) by 0 days.

(21) Appl. No.: 09/515,260

(22) Filed: Feb. 29, 2000

Related U.S. Application Data

(63) Continuation-in-part of application No. 09/456,693, filed on Dec. 9, 1999.
(60) Provisional application No. 60/111,737, filed on Dec. 10, 1998.

(51) Int. Cl.[7] ............................................. A61K 38/00
(52) U.S. Cl. ...................................... 435/69.1; 435/7.1
(58) Field of Search ............................. 435/7.1, 6, 7.4, 435/7.6, 7.8, 7.92, 69.1; 436/501; 514/2; 530/350, 810, 811, 812, 866

(56) References Cited

U.S. PATENT DOCUMENTS

| | | | |
|---|---|---|---|
| 5,235,041 A | 8/1993 | Cappello et al. | ............ 530/353 |
| 5,514,581 A | 5/1996 | Ferrari et al. | ............ 435/252.3 |
| 5,545,620 A | 8/1996 | Wahl et al. | .................... 514/12 |
| 5,641,648 A | 6/1997 | Ferrari et al. | ............... 435/69.1 |
| 5,770,697 A | 6/1998 | Ferrari et al. | ............... 530/353 |
| 5,792,742 A | 8/1998 | Gold et al. | ..................... 514/2 |
| 6,018,030 A | 1/2000 | Ferrari et al. | ............... 530/353 |
| 6,462,189 B1 | 10/2002 | Koide | |

FOREIGN PATENT DOCUMENTS

| | | |
|---|---|---|
| WO | WO 98/31700 | 7/1998 |
| WO | WO 98/56915 | 12/1998 |
| WO | WO 00/34784 | 6/2000 |

OTHER PUBLICATIONS

Wells, James, A. Additivity of Mutational Effects in Proteins, 1990, Biochemistry, vol. 29, pp. 509–8517.*
Ngo et al. "Computational Complexity, Protein Structure Prediction, and the Levinthal Paradox" in The Protein Folding Problem and Tertiary Structure Prediction, Merz & Le Grand, ed. Birkhauser, Boston, 1994, pp. 491–495.*
Lee et al. Strong Inhibition of fibrinogen binding to platelet receptor alpha llb/beta3 by RGD sequences installed into a presentation scaffold, 1993, Protein Engineering, vol. 6, pp. 745–754.*
Bianchi et al., "High Level Expression and Rational Mutagenesis of a Designed Protein, the Minibody," *J. Mol. Biol.* 236:649–659 (1994).
Muller et al., "Structure of the NF–kB p50 Homodimer Bound to DNA," Nature 373:311–317 (1995).

Nord et al., "Binding Proteins Selected From Combinatorial Libraries of an α–Helical Bacterial Receptor Domain," Nature Biotechnology 15:772–777 (1997).
Nord et al., "A Combinatorial Library of an α–Helical Bacterial Receptor Domain," Protein Eng. 8:601–608 (1995).
Nygren and Uhlen, "Scaffolds for Engineering Novel Binding Sites in Proteins," Current Opinion in Structural Biology 7:463–469 (1997).
Plaxco et al., "Rapid Refolding of a Proline–Rich All–β–Sheet Fibronectin," Proc. Natl. Acad. Sci. USA 93:10703–10706 (1996).
Potts and Campbell, "Fibronectin Structure and Assembly," Curr. Opin. Cell Biol. 6:648–655 (1994).
Roberts and Szostak, "RNA–Peptide Fusions for the In Vitro Selection of Peptides and Proteins," Proc. Natl. Acad. Sci. USA 94:12297–12302 (1997).
Rottgen and Collins, "A Human Pancreatic Secretory Trypsin Inhibitor Presenting a Hypervariable Highly Constrained Epitope Via Monovalent Phagemid Display," Gene 164:243–250 (1995).
Smith and Petrenko, "Phage Display," Chem. Rev. 97:391–410 (1997).
Tramontano et al., "The Making of the Minibody: An Engineered β–Protein for the Display of Conformationally Constrained Peptides," J. Molecular Recognition 7:9–24 (1994).
Wang et al., "Isolation of a High Affinity Inhibitor of Urokinase–Type Plasminogen Activator by Phage Display of Ecotin," J. Biol. Chem. 270:12250–12256 (1995).
Watanabe et al., "Gene Cloning of Chitinase A1 From Bacillus Circulans WL–12 Revealed Its Evolutionary Relationship to Serratia Chitinase and to the Type III Homology Units of Fibronectin," J. Biol. Chem. 265:15659–15665 (1990).
Williams and Barclay, "The Immunoglobulin Superfamily—Domains for Cell Surface Recognition," Ann. Rev. Immunol. 6:381–405 (1988).
Dickinson et al., "Crystal Structure of the Tenth Type III Cell Adhesion Module of Human Fibronectin," J. Mol. Biol. 236:1079–1092 (1994).
Ghosh et al., "Structure of NF–kB p50 Homodimer Bound to a kB Site," Nature 373:303–310 (1995).
Hamers–Casterman et al., "Naturally Occurring Antibodies Devoid of Light Chains," Nature 363:446–448 (1993).

(List continued on next page.)

*Primary Examiner*—Christopher R. Tate
*Assistant Examiner*—Maury Audet
(74) *Attorney, Agent, or Firm*—Ropes & Gray LLP

(57) ABSTRACT

Disclosed herein are proteins that include a fibronectin type III domain having at least one randomized loop. Also disclosed herein are nucleic acids encoding such proteins and the use of such proteins in diagnostic methods and in methods for evolving novel compound-binding species and their ligands.

22 Claims, 15 Drawing Sheets

OTHER PUBLICATIONS

Hynes, "Integrins: Versatility, Modulation, and Signaling in Cell Adhesion," Cell 69:11–25 (1992).

Kohler and Milstein, "Continuous Cultures of Fused Cells Secreting Antibody of Predefined Specificity," Nature 256:495–497 (1975).

Ku and Schultz, "Alternate Protein Frameworks for Molecular Recognition," Proc. Natl. Acad. Sci. USA 92:6552–6556 (1995).

Leahy et al., "Structure of a Fibronectin Type III Domain from Tenascin Phased by MAD Analysis of the Selenomethionyl Protein," Science 258:987–991 (1992).

Litvinovich and Ingham, "Interactions Between Type III Domains in the 110 kDa Cell–Binding Fragment of Fibronectin," J. Mol. Biol. 248:611–626 (1995).

Main et al., "The Three–Dimensional Structure of the Tenth Type III Module of Fibronectin: An Insight into RGD–Mediated Interactions," Cell 71:671–678 (1992).

Markland et al., "Iterative Optimization of High–Affinity Protease Inhibitors Using Phage Display. 1. Plasmin," Biochemistry 35:8045–8057 (1996).

Markland et al., "Iterative Optimization of High–Affinity Protease Inhibitors Using Phage Display. 2. Plasma Kallikrein and Thrombin," Biochemistry 35:8058–8067 (1996).

McConnell and Hoess, "Tendamistat as a Scaffold for Conformationally Constrained Phage Peptide Libraries," J. Mol. Biol. 250:460–470 (1995).

Meinke et al., "Cellulose–Binding Polypeptides from Cellulomonas fimi: Endoglucanase D (CenD), a Family A β–1,4–Glucanase," J. Bacteriology 175:1910–1918 (1993).

Baron et al., "H NMR Assignment and Secondary Structure of the Cell Adhesion Type III Module of Fibronectin," Biochemistry 31:2068–2073 (1992).

Boder et al., "Yeast Surface Display for Screening Combinatorial Polypeptide Libraries," Nature Biotechnology 15:553–557 (1997).

Bork and Doolittle, "Proposed Acquisition of an Animal Protein Domain by Bacteria," Proc. Natl. Acad. Sci. USA 89:8990–8994 (1992).

Clackson and Wells, "In Vitro Selection from Protein and Peptide Libraries," TIBTECH 12:173–184 (1994).

Clackson et al., "Making Antibody Fragments Using Phage Display Libraries," Nature 352:624–628 (1991).

Koide et al., "Directed Evolution of Fibronectin Type III Domain to Novel Ligand Binding Proteins," *Combinatorial Approaches* Abstract M40 FASEB J. vol. 11, No. 9, pp. A837.

Koide et al., "Directed Evolution of Fibronectin Type III Domain to Novel Ligand Binding Proteins," *Designing Small and Large Molecules I* Abstract 1739 FASEBJ. vol. 11, No. 9, pp. A1155.

Lombardo et al., "Conformational Flexibility and Crystallization of Tandemly Linked Type III Modules of Human Fibronectin," Protein Sci 5:1934–1938 (1996).

Plaxco et al., "A Comparison of the Folding Kinetics and Thermodynamics of Two Homologous Fibronectin Type III Modules," J. Mol. Biol. 270:763–770 (1997).

Potts and Campbell, "Structure and Function of Fibronectin Modules," Matrix Biology 15:313–320 (1996).

Potts and Campbell, "Fibronectin Structure and Assembly," Curr. Opin. Cell Biol. 6:648–655 (1994).

Shibata et al., "An Attempt to Substitute the Cell Binding Domain of Human Fibronectin in Lambda Phage J Protein: Computer Design and Expression," Biochimie 75:459–465 (1993).

Williams et al., "Solution Structures of Modular Proteins by Nuclear Magnetic Resonance," Methods Enzymol 245:451–469 (1994).

Campbell et al., "Building Proteins with Fibronectin Type III Modules," Structure 2:333–337 (1994).

Clarke et al., "Folding and Stability of a Fibronectin Type III Domain of Human Tenascin," J. Mol. Biol. 270:771–778 (1997).

Copie et al., "Solution Structure and Dynamics of Linked Cell Attachment Modules of Mouse Fibronectin Containing the RGD and Synergy Regions: Comparison with the Human Fibronectin Crystal Structure," J. Mol. Biol. 277:663–682 (1998).

Dickinson et al., "Crystals of the Cell–Binding Module of Fibronectin Obtained From a Series of Recombinant Fragments Differing in Length," J. Mol. Biol. 238:123–127 (1994).

Ely et al., "Common Molecular Scaffold for Two Unrelated RGD Molecules," Protein Eng 8:823–827 (1995).

Grant et al., "Structural Requirements for Biological Activity of the Ninth and Tenth FIII Domains of Human Fibronectin," J. Biol. Chem. 272:6159–6166 (1997).

Hocking et al., "A Novel Role for the Integrin–Binding III–10 Module in Fibronectin Matrix Assembly," The Journal of Cell Biology 133:431–444 (1996).

Hocking et al., "Activation of Distinct $\alpha_5\beta_1$–Mediated Signaling Pathways by Fibronectin's Cell Adhesion and Matrix Assembly Domains," The Journal of Cell Biology 141:241–253 (1998).

Koide et al., "The Fibronectin Type III Domain as a Scaffold for Novel Binding Proteins," J. Mol. Biol. 284:1141–1151 (1998).

* cited by examiner

|  |  | 1 | 9 10 | 19 20 | 29 30 | 37 38 | 47 48 | 57 58 | 67 68 | 77 78 | 87 88 |  |
|---|---|---|---|---|---|---|---|---|---|---|---|---|
| Hs | FND | VSDVPRD-LE | VVAATPTSLL | ISWDAPAVTV | RYRITYG-- | ETGGNSPVQE | FTVPGSKSTA | TISGLKPGVD | YTITVYAVTG | RGDSPASSKP | ISINYRT | 94 |
| Bt | FN  | VSDVPRD-LE | VIAATPTSLL | ISWDAPAVTV | RYRITYG-- | ETGGSSPVQE | FTVPGSKSTA | TISGLKPGVD | YTITVYAVTG | RGDSPASSKP | VSINYRT | 94 |
| Rn | FN  | VSDVPRD-LE | VIASTPTSLL | ISWEpPAVSV | RYRITYG-- | ETGGNSPVQE | FTVPGSKSTA | TINnIKPGAD | YTITLYAVTG | RGDSPASSKP | VSINYQI | 1510 |
| Mm | FN  | VSDIPRD-LE | VIASTPTSLL | ISWEpPAVSV | RYRITYG-- | ETGGNSPVQE | FTVPGSKSTA | TINnIKPGAD | YTITLYAVTG | RGDSPASSKP | VSINYKT | 1611 |
| Oc | FN  | VSDVPRD-LE | VIASTPTSLL | ISWEXPAVTV | RYRITYG-- | ETppN---- | --------- | ---------- | ---------- | ---------- | ------- | 712 |
| Gg | FN  | VSDVPRD-LE | VNpTSPTSLE | ISWEAPAVTV | RYRITYS-- | ETGGSSPVQE | FTVPGTMSrA | TITGLKPGVD | YTITVYAVTG | RGDSPASSKP | VTVTYKT | 64 |
| Xl | FN  | VSDVPTD-LE | VTSSSPNTLT | ISWEAPAVSV | RYRITYS-- | QTGGhGPEKE | FTVPGTSNTA | TIRGLNPGVS | YTITVYAVTG | RGDSPASSKP | LTIIHKT | 443 |
| Cf | FN  | AiDAPSn-Lr | FLATTPnSLL | VSWQpPrArI | TGYIIKye-- | kpGSpprEVV | prprPGVTeA | TITGLePGTE | YTIQVIALKn | NQKSepLIGr | kKTdEL- | 1611 |
| Ec | FN  | AiDAPSn-Lh | FLATTPnSLL | ISWQpPrArI | TGYIIKye-- | kpGSpprEVV | prphPGVTeA | TITGLePGTE | YTIQVIALKn | NQKSepLIGr | rKTdEp- | 197 |
| Hs | TC  | VS-PPKD-Lv | VTeVTeeTVN | LAWDn-eMrV | TeYLVVYTP- | -THEGGlEMQ | FrVPGDQTST | IIQeLePGVE | YFIRVPAlLe | NKKSipVSAr | V------ | 197 |
| Ss | TP  | VS-PPKD-Li | VTeVTeeTVN | LAWDn-eMrV | TeYLIVYTP- | -THEDGlEMQ | FrVPGDQTST | TIReLePGVE | YFIRVPAlLe | NKKSipVSAr | V------ | 686 |
| Mm | TX  | MiDGPQD-Lr | VVAVTPTTLD | LSWlrPQAeV | DrFVVSYV-- | --SAGNqRVr | LeVPPEADrT | QLTdlMPGVE | YVVTVAERG | HAVSypASIr | ANTG--- | 686 |
| Hs | CAP | TlpVPvvSln | IYdVGPTTMH | VQWQP-VGGA | TGYILSYkPV | kDTEpTrpKE | VrLGPTVNdM | QLTdlVPNTE | YAVTVQAVLh | dLTSepVTVr | e------ | 889 |
| Oc | C12 | TlpVPvvSLN | IYdVGPTTMH | VQWQP-VGGA | TGYILSYkPV | kDTEpTrpKp | QdVkLRdVTH | ---------- | ---------- | ---------- | ------- | 1551 |
| Gg | C14 | LalpmaSDLk | LYdVShSSMR | AKWnG-VAGA | TGYMILYAPL | TEGLAadEKE | IkIGEASTeL | BLDGLLPNTE | YTVTVYAMF- | ---------- | ------- | 322 |
| Hs | U1  | LalpmaSDll | LYdVTenSMR | VKWDA-VpGA | SGYILIYAPL | TEGLAGdEKE | MkIGETHTdi | BLSGLLPNTE | YTVTVYAMFG | eeASDpVTGq | e------ | 508 |

| var. |   |   |   |   |   |   |   |   |   |   |   |
|---|---|---|---|---|---|---|---|---|---|---|---|
| cons. | P | W | V | Y I Y | | I | L PGVD Y ITV A | G | | | P |
|      | L | SL | A |   F V | |   | NTE VQL | N | | S | R |
|      | M | TV | I |     L | | L | AS R | E | | | |
|      |   | M  |   |       | |   |        |   | | | |

CAP Collagen alpha precursor
C12 Collagen type 12
FND Fibronectin type III domain
FN Fibronectin
TP Tenascin precursor
TC Tenascin-C
U1 Undulin 1

Bt Bovis taurus          cow
Cf Canis familiaris      dog
Ec Equus caballis        horse
Ss Sus scrofa            pig
Hs Homo sapiens          human
Oc Oryctolagus cuniculus rabbit
Xl Xenupus laevis        African clawed frog BOLD        identical to Hs FND
lower case  non-conservative substitution
            (charge reversal, change between hydrophobic
            and charged, addition or removal of P)
-           position of non-conservative substitutions

Fig. 4

PROTEIN SCAFFOLDS FOR ANTIBODY MIMICS AND OTHER BINDING PROTEINS

CROSS REFERENCE TO RELATED APPLICATIONS

This application is a continuation-in-part of utility application, U.S. Ser. No. 09/456,693, filed Dec. 9, 1999, which claims the benefit of the filing date of provisional application, U.S. Ser. No. 60/111,737, filed Dec. 10, 1998, now abandoned.

BACKGROUND OF THE INVENTION

This invention relates to protein scaffolds useful, for example, for the generation of products having novel binding characteristics.

Proteins having relatively defined three-dimensional structures, commonly referred to as protein scaffolds, may be used as reagents for the design of engineered products. These scaffolds typically contain one or more regions which are amenable to specific or random sequence variation, and such sequence randomization is often carried out to produce libraries of proteins from which desired products may be selected. One particular area in which such scaffolds are useful is the field of antibody design.

A number of previous approaches to the manipulation of the mammalian immune system to obtain reagents or drugs have been attempted. These have included injecting animals with antigens of interest to obtain mixtures of polyclonal antibodies reactive against specific antigens, production of monoclonal antibodies in hybridoma cell culture (Koehler and Milstein, Nature 256:495, 1975), modification of existing monoclonal antibodies to obtain new or optimized recognition properties, creation of novel antibody fragments with desirable binding characteristics, and randomization of single chain antibodies (created by connecting the variable regions of the heavy and light chains of antibody molecules with a flexible peptide linker) followed by selection for antigen binding by phage display (Clackson et al., Nature 352:624, 1991).

In addition, several non-immunoglobulin protein scaffolds have been proposed for obtaining proteins with novel binding properties. For example, a "minibody" scaffold, which is related to the immunoglobulin fold, has been designed by deleting three beta strands from a heavy chain variable domain of a monoclonal antibody (Tramontano et al., J. Mol. Recognit. 7:9, 1994). This protein includes 61 residues and can be used to present two hypervariable loops. These two loops have been randomized and products selected for antigen binding, but thus far the framework appears to have somewhat limited utility due to solubility problems. Another framework used to display loops has been tendamistat, a 74 residue, six-strand beta sheet sandwich held together by two disulfide bonds (McConnell and Hoess, J. Mol. Biol. 250:460, 1995). This scaffold includes three loops, but, to date, only two of these loops have been examined for randomization potential.

Other proteins have been tested as frameworks and have been used to display randomized residues on alpha helical surfaces (Nord et al., Nat. Biotechnol. 15:772, 1997; Nord et al., Protein Eng. 8:601, 1995), loops between alpha helices in alpha helix bundles (Ku and Schultz, Proc. Natl. Acad. Sci. USA 92:6552, 1995), and loops constrained by disulfide bridges, such as those of the small protease inhibitors (Markland et al., Biochemistry 35:8045, 1996; Markland et al., Biochemistry 35:8058, 1996; Rottgen and Collins, Gene 164:243, 1995; Wang et al., J. Biol. Chem. 270:12250, 1995).

SUMMARY OF THE INVENTION

The present invention provides a new family of proteins capable of evolving to bind any compound of interest. These proteins, which make use of a fibronectin or fibronectin-like scaffold, function in a manner characteristic of natural or engineered antibodies (that is, polyclonal, monoclonal, or single-chain antibodies) and, in addition, possess structural advantages. Specifically, the structure of these antibody mimics has been designed for optimal folding, stability, and solubility, even under conditions which normally lead to the loss of structure and function in antibodies.

These antibody mimics may be utilized for the purpose of designing proteins which are capable of binding to virtually any compound (for example, any protein) of interest. In particular, the fibronectin-based molecules described herein may be used as scaffolds which are subjected to directed evolution designed to randomize one or more of the three fibronectin loops which are analogous to the complementarity-determining regions (CDRs) of an antibody variable region. Such a directed evolution approach results in the production of antibody-like molecules with high affinities for antigens of interest. In addition, the scaffolds described herein may be used to display defined exposed loops (for example, loops previously randomized and selected on the basis of antigen binding) in order to direct the evolution of molecules that bind to such introduced loops. A selection of this type may be carried out to identify recognition molecules for any individual CDR-like loop or, alternatively, for the recognition of two or all three CDR-like loops combined into a non-linear epitope.

Accordingly, the present invention features a protein that includes a fibronectin type III domain having at least one randomized loop, the protein being characterized by its ability to bind to a compound that is not bound by the corresponding naturally-occurring fibronectin.

In preferred embodiments, the fibronectin type III domain is a mammalian (for example, a human) fibronectin type III domain; and the protein includes the tenth module of the fibronectin type III ($^{10}$Fn3) domain. In such proteins, compound binding is preferably mediated by either one, two, or three $^{10}$Fn3 loops. In other preferred embodiments, the second loop of $^{10}$Fn3 may be extended in length relative to the naturally-occurring module, or the $^{10}$Fn3 may lack an integrin-binding motif. In these molecules, the integrin-binding motif may be replaced by an amino acid sequence in which a basic amino acid-neutral amino acid-acidic amino acid sequence (in the N-terminal to C-terminal direction) replaces the integrin-binding motif; one preferred sequence is serine-glycine-glutamate. In another preferred embodiment, the fibronectin type III domain-containing proteins of the invention lack disulfide bonds.

Any of the fibronectin type III domain-containing proteins described herein may be formulated as part of a fusion protein (for example, a fusion protein which further includes an immunoglobulin $F_c$ domain, a complement protein, a toxin protein, or an albumin protein). In addition, any of the fibronectin type III domain proteins may be covalently bound to a nucleic acid (for example, an RNA), and the nucleic acid may encode the protein. Moreover, the protein may be a multimer, or, particularly if it lacks an integrin-binding motif, it may be formulated in a physiologically-acceptable carrier.

The present invention also features proteins that include a fibronectin type III domain having at least one mutation in a β-sheet sequence which changes the scaffold structure. Again, these proteins are characterized by their ability to bind to compounds that are not bound by the corresponding naturally-occurring fibronectin.

In addition, any of the fibronectin scaffolds of the invention may be immobilized on a solid support (for example, a bead or chip), and these scaffolds may be arranged in any configuration on the solid support, including an array.

In a related aspect, the invention further features nucleic acids encoding any of the proteins of the invention. In preferred embodiments, the nucleic acid is DNA or RNA.

In another related aspect, the invention also features a method for generating a protein which includes a fibronectin type III domain and which is pharmaceutically acceptable to a mammal, involving removing the integrin-binding domain of said fibronectin type III domain. This method may be applied to any of the fibronectin type III domain-containing proteins described above and is particularly useful for generating proteins for human therapeutic applications. The invention also features such fibronectin type III domain-containing proteins which lack integrin-binding domains.

In yet other related aspects, the invention features screening methods which may be used to obtain or evolve randomized fibronectin type III proteins capable of binding to compounds of interest, or to obtain or evolve compounds (for example, proteins) capable of binding to a particular protein containing a randomized fibronectin type III motif. In addition, the invention features screening procedures which combine these two methods, in any order, to obtain either compounds or proteins of interest.

In particular, the first screening method, useful for the isolation or identification of randomized proteins of interest, involves: (a) contacting the compound with a candidate protein, the candidate protein including a fibronectin type III domain having at least one randomized loop, the contacting being carried out under conditions that allow compound-protein complex formation; and (b) obtaining, from the complex, the protein which binds to the compound.

The second screening method, for isolating or identifying a compound which binds to a protein having a randomized fibronectin type III domain, involves: (a) contacting the protein with a candidate compound, the contacting being carried out under conditions that allow compound-protein complex formation; and (b) obtaining, from the complex, the compound which binds to the protein.

In preferred embodiments, the methods further involve either randomizing at least one loop of the fibronectin type III domain of the protein obtained in step (b) and repeating steps (a) and (b) using the further randomized protein, or modifying the compound obtained in step (b) and repeating steps (a) and (b) using the further modified compound. In addition, the compound is preferably a protein, and the fibronectin type III domain is preferably a mammalian (for example, a human) fibronectin type III domain. In other preferred embodiments, the protein includes the tenth module of the fibronectin type III domain ($^{10}$Fn3), and binding is mediated by one, two, or three $^{10}$Fn3 loops. In addition, the second loop of $^{10}$Fn3 may be extended in length relative to the naturally-occurring module, or $^{10}$Fn3 may lack an integrin-binding motif. Again, as described above, the integrin-binding motif may be replaced by an amino acid sequence in which a basic amino acid-neutral amino acid-acidic amino acid sequence (in the N-terminal to C-terminal direction) replaces the integrin-binding motif; one preferred sequence is serine-glycine-glutamate.

The selection methods described herein may be carried out using any fibronectin type III domain-containing protein. For example, the fibronectin type III domain-containing protein may lack disulfide bonds, or may be formulated as part of a fusion protein (for example, a fusion protein which further includes an immunoglobulin $F_c$ domain, a complement protein, a toxin protein, or an albumin protein). In addition, selections may be carried out using the fibronectin type III domain proteins covalently bound to nucleic acids (for example, RNAs or any nucleic acid which encodes the protein). Moreover, the selections may be carried out using fibronectin domain-containing protein multimers.

Preferably, the selections involve the immobilization of the binding target on a solid support. Preferred solid supports include columns (for example, affinity columns, such as agarose columns) or microchips.

In addition, the invention features diagnostic methods which employ the fibronectin scaffold proteins of the invention. Such diagnostic methods may be carried out on a sample (for example, a biological sample) to detect one analyte or to simultaneously detect many different analytes in the sample. The method may employ any of the scaffold molecules described herein. Preferably, the method involves (a) contacting the sample with a protein which binds to the compound analyte and which includes a fibronectin type III domain having at least one randomized loop, the contacting being carried out under conditions that allow compound-protein complex formation; and (b) detecting the complex, and therefore the compound in the sample.

In preferred embodiments, the protein is immobilized on a solid support (for example, a chip or bead) and may be immobilized as part of an array. The protein may be covalently bound to a nucleic acid, preferably, a nucleic acid, such as RNA, that encodes the protein. In addition, the compound is often a protein, but may also be any other analyte in a sample. Detection may be accomplished by any standard technique including, without limitation, radiography, fluorescence detection, mass spectroscopy, or surface plasmon resonance.

As used herein, by "fibronectin type III domain" is meant a domain having 7 or 8 beta strands which are distributed between two beta sheets, which themselves pack against each other to form the core of the protein, and further containing loops which connect the beta strands to each other and are solvent exposed. There are at least three such loops at each edge of the beta sheet sandwich, where the edge is the boundary of the protein perpendicular to the direction of the beta strands. Preferably, a fibronectin type III domain includes a sequence which exhibits at least 30% amino acid identity, and preferably at least 50% amino acid identity, to the sequence encoding the structure of the $^{10}$Fn3 domain referred to as "1ttg" (ID="1ttg" (one ttg)) available from the Protein Data Base. Sequence identity referred to in this definition is determined by the Homology program, available from Molecular Simulation (San Diego, Calif.). The invention further includes polymers of $^{10}$Fn3-related molecules, which are an extension of the use of the monomer structure, whether or not the subunits of the polyprotein are identical or different in sequence.

By "naturally occurring fibronectin" is meant any fibronectin protein that is encoded by a living organism.

By "randomized" is meant including one or more amino acid alterations relative to a template sequence.

By a "protein" is meant any sequence of two or more amino acids, regardless of length, post-translation modification, or function. "Protein" and "peptide" are used interchangeably herein.

By "RNA" is meant a sequence of two or more covalently bonded, naturally occurring or modified ribonucleotides.

One example of a modified RNA included within this term is phosphorothioate RNA.

By "DNA" is meant a sequence of two or more covalently bonded, naturally occurring or modified deoxyribonucleotides.

By a "nucleic acid" is meant any two or more covalently bonded nucleotides or nucleotide analogs or derivatives. As used herein, this term includes, without limitation, DNA, RNA, and PNA.

By "pharmaceutically acceptable" is meant a compound or protein that may be administered to an animal (for example, a mammal) without significant adverse medical consequences.

By "physiologically acceptable carrier" is meant a carrier which does not have a significant detrimental impact on the treated host and which retains the therapeutic properties of the compound with which it is administered. One exemplary physiologically acceptable carrier is physiological saline. Other physiologically acceptable carriers and their formulations are known to one skilled in the art and are described, for example, in *Remington's Pharmaceutical Sciences*, (18$^{th}$ edition), ed. A. Gennaro, 1990, Mack Publishing Company, Easton, Pa., incorporated herein by reference.

By "selecting" is meant substantially partitioning a molecule from other molecules in a population. As used herein, a "selecting" step provides at least a 2-fold, preferably, a 30-fold, more preferably, a 100-fold, and, most preferably, a 1000-fold enrichment of a desired molecule relative to undesired molecules in a population following the selection step. A selection step may be repeated any number of times, and different types of selection steps may be combined in a given approach.

By "binding partner," as used herein, is meant any molecule which has a specific, covalent or non-covalent affinity for a portion of a desired compound (for example, protein) of interest. Examples of binding partners include, without limitation, members of antigen/antibody pairs, protein/inhibitor pairs, receptor/ligand pairs (for example cell surface receptor/ligand pairs, such as hormone receptor/peptide hormone pairs), enzyme/substrate pairs (for example, kinase/substrate pairs), lectin/carbohydrate pairs, oligomeric or heterooligomeric protein aggregates, DNA binding protein/DNA binding site pairs, RNA/protein pairs, and nucleic acid duplexes, heteroduplexes, or ligated strands, as well as any molecule which is capable of forming one or more covalent or non-covalent bonds (for example, disulfide bonds) with any portion of another molecule (for example, a compound or protein).

By a "solid support" is meant, without limitation, any column (or column material), bead, test tube, microtiter dish, solid particle (for example, agarose or sepharose), microchip (for example, silicon, silicon-glass, or gold chip), or membrane (for example, the membrane of a liposome or vesicle) to which a fibronectin scaffold or an affinity complex may be bound, either directly or indirectly (for example, through other binding partner intermediates such as other antibodies or Protein A), or in which a fibronectin scaffold or an affinity complex may be embedded (for example, through a receptor or channel).

The present invention provides a number of advantages. For example, as described in more detail below, the present antibody mimics exhibit improved biophysical properties, such as stability under reducing conditions and solubility at high concentrations. In addition, these molecules may be readily expressed and folded in prokaryotic systems, such as E. coli, in eukaryotic systems, such as yeast, and in vitro translation systems, such as the rabbit reticulocyte lysate system. Moreover, these molecules are extremely amenable to affinity maturation techniques involving multiple cycles of selection, including in vitro selection using RNA-protein fusion technology (Roberts and Szostak, Proc. Natl. Acad. Sci USA 94:12297, 1997; Szostak et al., U.S. Ser. No. 09/007,005, now U.S. Pat. No. 6,258,558 B1 and U.S. Ser. No. 09/247,190, now U.S. Pat. No. 6,261,804 B1; Szostak et al. WO98/31700), phage display (see, for example, Smith and Petrenko, Chem. Rev. 97:317, 1997), and yeast display systems (see, for example, Boder and Wittrup, Nature Biotech. 15:553, 1997).

Other features and advantages of the present invention will be apparent from the following detailed description thereof, and from the claims.

BRIEF DESCRIPTION OF THE DRAWINGS

FIG. 4 is a graph illustrating a sequence alignment between a fibronectin type III protein domain and related protein domains.

DETAILED DESCRIPTION

The novel antibody mimics described herein have been designed to be superior both to antibody-derived fragments and to non-antibody frameworks, for example, those frameworks described above.

The major advantage of these antibody mimics over antibody fragments is structural. These scaffolds are derived from whole, stable, and soluble structural modules found in human body fluid proteins. Consequently, they exhibit better folding and thermostability properties than antibody fragments, whose creation involves the removal of parts of the antibody native fold, often exposing amino acid residues that, in an intact antibody, would be buried in a hydrophobic environment, such as an interface between variable and constant domains. Exposure of such hydrophobic residues to solvent increases the likelihood of aggregation.

In addition, the antibody mimics described herein have no disulfide bonds, which have been reported to retard or prevent proper folding of antibody fragments under certain conditions. Since the present scaffolds do not rely on disulfides for native fold stability, they are stable under reducing conditions, unlike antibodies and their fragments which unravel upon disulfide bond breakdown.

Moreover, these fibronectin-based scaffolds provide the functional advantages of antibody molecules. In particular, despite the fact that the $^{10}$Fn3 module is not an immunoglobulin, its overall fold is close to that of the variable region of the IgG heavy chain (FIG. 2), making it possible to display the three fibronectin loops analogous to CDRs in relative orientations similar to those of native antibodies. Because of this structure, the present antibody mimics possess antigen binding properties that are similar in nature and affinity to those of antibodies, and a loop randomization and shuffling strategy may be employed in vitro that is similar to the process of affinity maturation of antibodies in vivo.

There are now described below exemplary fibronectin-based scaffolds and their use for identifying, selecting, and evolving novel binding proteins as well as their target ligands. These examples are provided for the purpose of illustrating, and not limiting, the invention.

$^{10}$Fn3 Structural Motif

Figure 1:
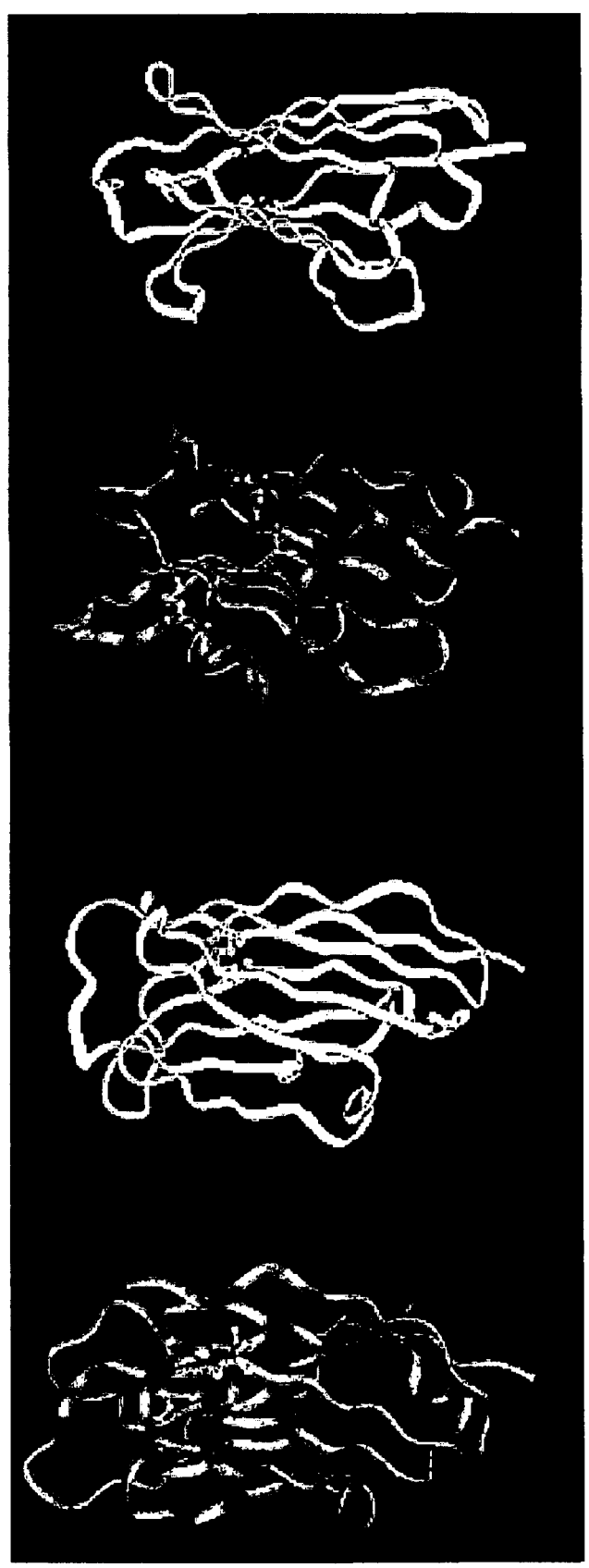
FIG. 1 is a photograph showing a comparison between the structures of antibody heavy chain variable regions from camel (dark blue) and llama (light blue), in each of two orientations.
Figure 2:
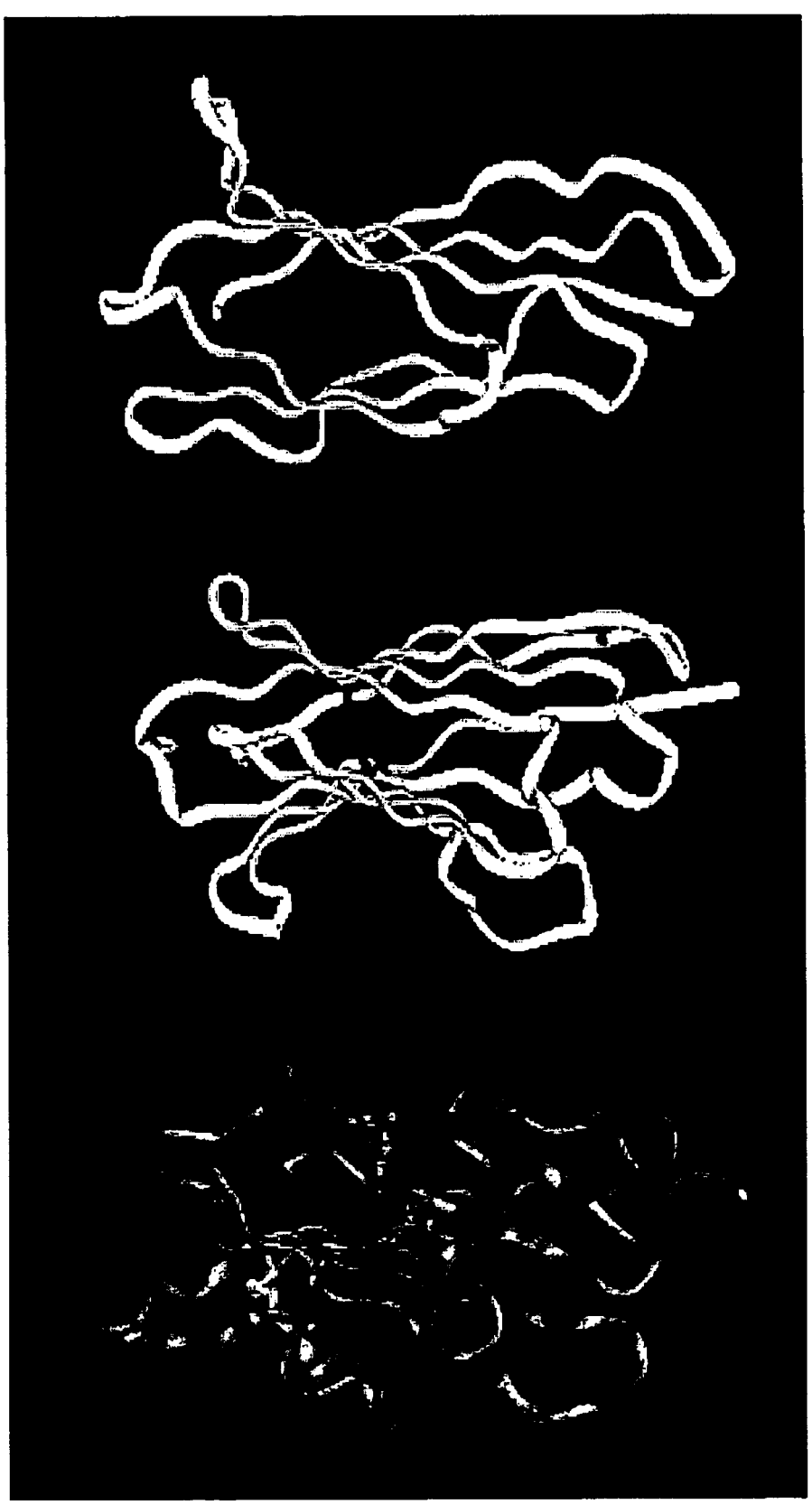
FIG. 2 is a photograph showing a comparison between the structures of the camel antibody heavy chain variable region (dark blue), the llama antibody heavy chain variable region (light blue), and a fibronectin type III module number 10 ($^{10}$Fn3) (yellow).

The antibody mimics of the present invention are based on the structure of a fibronectin module of type III (Fn3), a common domain found in mammalian blood and structural proteins. This domain occurs more than 400 times in the protein sequence database and has been estimated to occur in 2% of the proteins sequenced to date, including fibronectins, tenascin, intracellular cytoskeletal proteins, and prokaryotic enzymes (Bork and Doolittle, Proc. Natl. Acad. Sci. USA 89:8990, 1992; Bork et al., Nature Biotech. 15:553, 1997; Meinke et al., J. Bacteriol. 175:1910, 1993; Watanabe et al., J. Biol. Chem. 265:15659, 1990). In particular, these scaffolds include, as templates, the tenth module of human Fn3 ($^{10}$Fn3), which comprises 94 amino acid residues. The overall fold of this domain is closely related to that of the smallest functional antibody fragment, the variable region of the heavy chain, which comprises the entire antigen recognition unit in camel and llama IgG (FIGS. 1, 2). The major differences between camel and llama domains and the $^{10}$Fn3 domain are that (i) $^{10}$F3 has fewer beta strands (seven vs. nine) and (ii) the two beta sheets packed against each other are connected by a disulfide bridge in the camel and llama domains, but not in $^{10}$F3.

Figure 3:
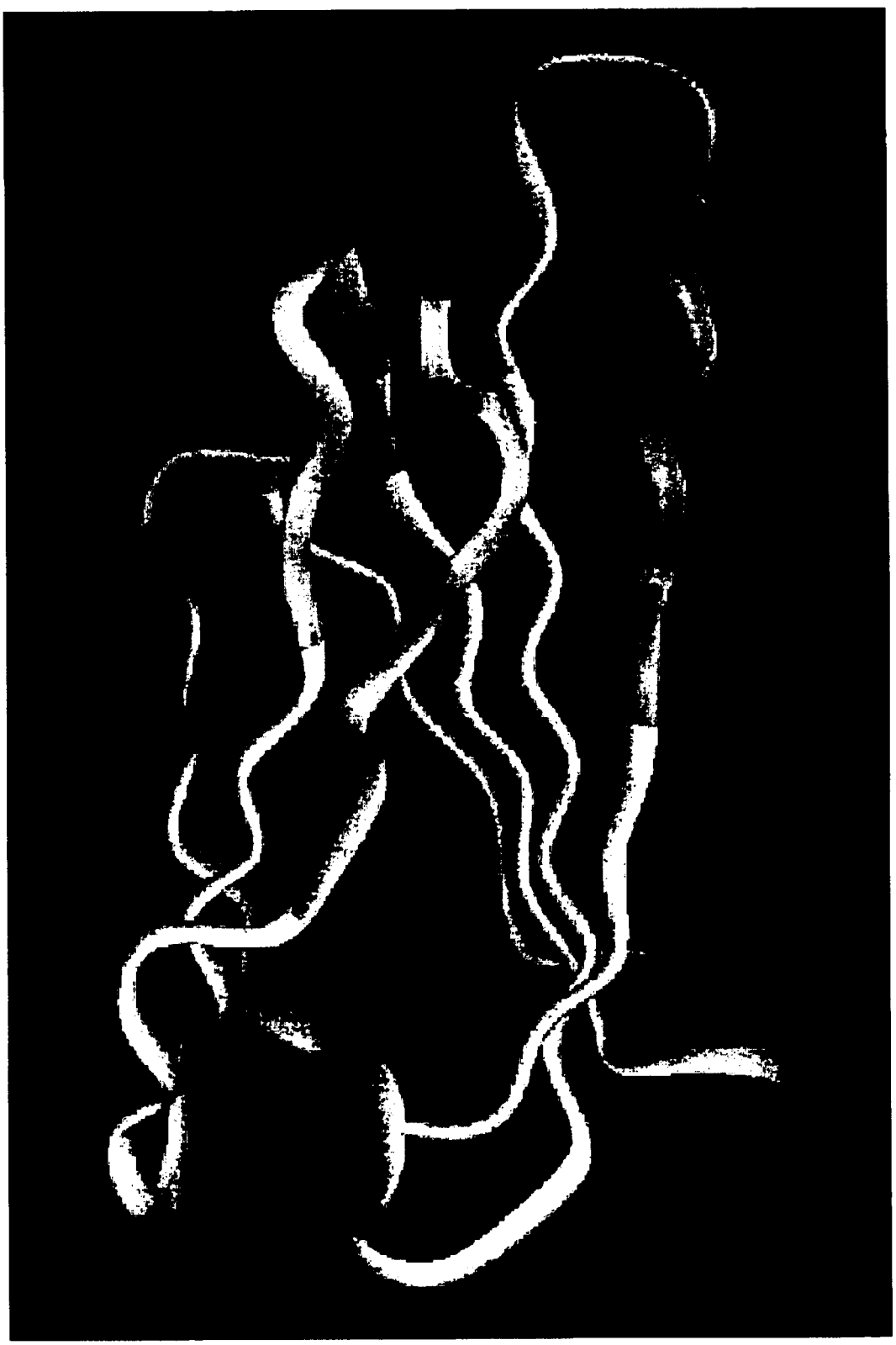
FIG. 3 is a photograph showing a fibronectin type III module number 10 ($^{10}$Fn3), with the loops corresponding to the antigen-binding loops in IgG heavy chains highlighted in red.

The three loops of $^{10}$Fn3 corresponding to the antigen-binding loops of the IgG heavy chain run between amino acid residues 21–31, 51–56, and 76–88 (FIG. 3). The length of the first and the third loop, 11 and 12 residues, respectively, fall within the range of the corresponding antigen-recognition loops found in antibody heavy chains, that is, 10–12 and 3–25 residues, respectively. Accordingly, once randomized and selected for high antigen affinity, these two loops make contacts with antigens equivalent to the contacts of the corresponding loops in antibodies.

In contrast, the second loop of $^{10}$Fn3 is only 6 residues long, whereas the corresponding loop in antibody heavy chains ranges from 16–19 residues. To optimize antigen binding, therefore, the second loop of $^{10}$Fn3 is preferably extended by 10–13 residues (in addition to being randomized) to obtain the greatest possible flexibility and affinity in antigen binding. Indeed, in general, the lengths as well as the sequences of the CDR-like loops of the antibody mimics may be randomized during in vitro or in vivo affinity maturation (as described in more detail below).

The tenth human fibronectin type III domain, $^{10}$Fn3, refolds rapidly even at low temperature; its backbone conformation has been recovered within 1 second at 5° C. Thermodynamic stability of $^{10}$Fn3 is high ($\Delta G_U$=24 kJ/mol= 5.7 kcal/mol), correlating with its high melting temperature of 110° C.

One of the physiological roles of $^{10}$Fn3 is as a subunit of fibronectin, a glycoprotein that exists in a soluble form in body fluids and in an insoluble form in the extracellular matrix (Dickinson et al., J. Mol. Biol. 236:1079, 1994). A fibronectin monomer of 220–250 kD contains 12 type I modules, two type II modules, and 17 fibronectin type III modules (Potts and Campbell, Curr. Opin.Cell Biol. 6:648, 1994). Different type III modules are involved in the binding of fibronectin to integrins, heparin, and chondroitin sulfate. $^{10}$Fn3 was found to mediate cell adhesion through an integrin-binding Arg-Gly-Asp (RGD) motif on one of its exposed loops. Similar RGD motifs have been shown to be involved in integrin binding by other proteins, such as fibrinogen, von Wellebrand factor, and vitronectin (Hynes et al., Cell 69:11, 1992). No other matrix- or cell-binding roles have been described for $^{10}$Fn3.

The observation that $^{10}$Fn3 has only slightly more adhesive activity than a short peptide containing RGD is consistent with the conclusion that the cell-binding activity of $^{10}$Fn3 is localized in the RGD peptide rather than distributed throughout the $^{10}$Fn3 structure (Baron et al., Biochemistry 31:2068, 1992). The fact that $^{10}$Fn3 without the RGD motif is unlikely to bind to other plasma proteins or extracellular matrix makes $^{10}$Fn3 a useful scaffold to replace antibodies. In addition, the presence of $^{10}$Fn3 in natural fibrinogen in the bloodstream suggests that $^{10}$Fn3 itself is unlikely to be immunogenic in the organism of origin.

Figure 5:
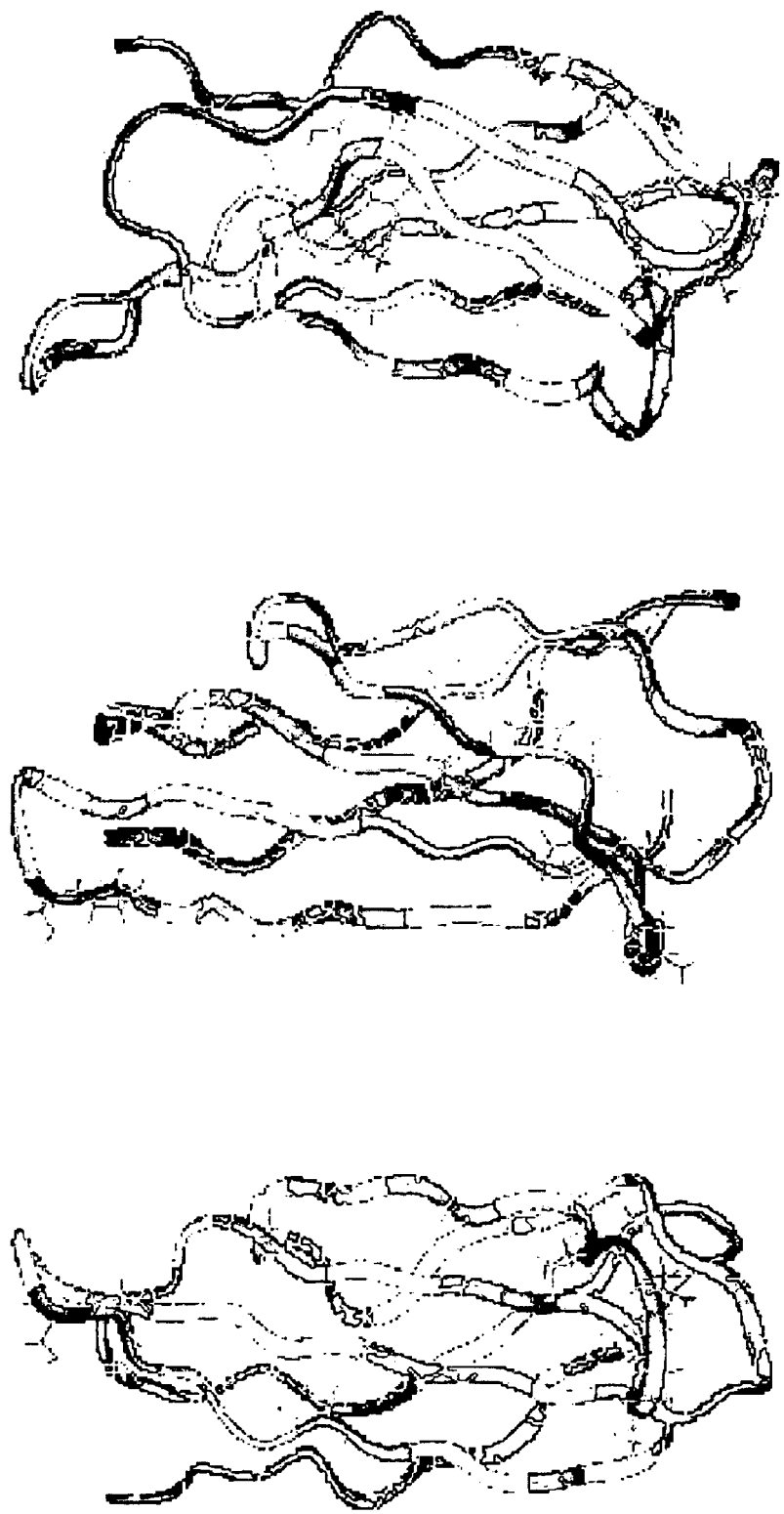
FIG. 5 is a photograph showing the structural similarities between a $^{10}$Fn3 domain and 15 related proteins, including fibronectins, tenascins, collagens, and undulin. In this photograph, the regions are labeled as follows: constant, dark blue; conserved, light blue; neutral, white; variable, red; and RGD integrin-binding motif (variable), yellow.
Figure 6:
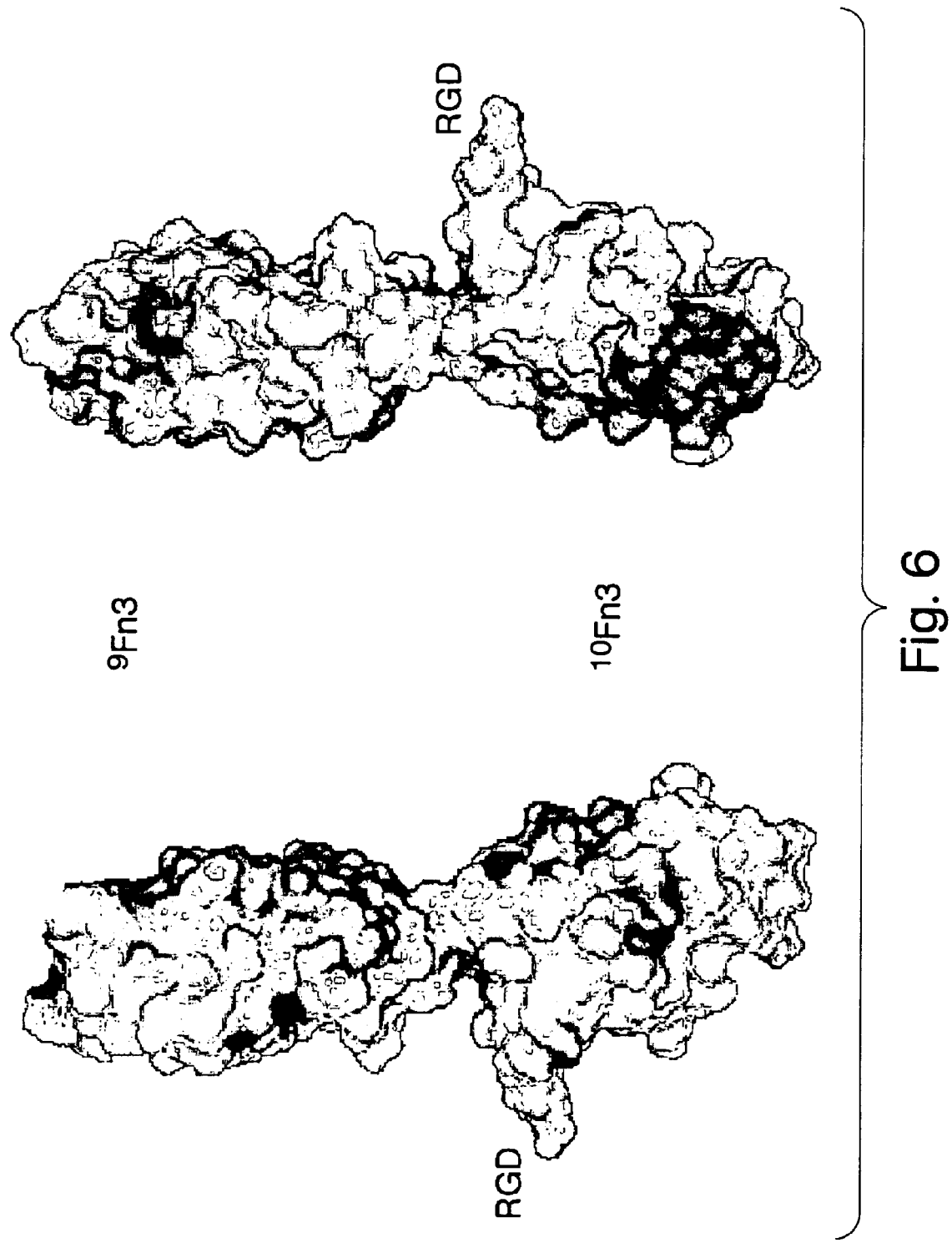
FIG. 6 is a photograph showing space filling models of fibronectin III modules 9 and 10, in each of two different orientations. The two modules and the integrin binding loop (RGD) are labeled. In this figure, blue indicates positively charged residues, red indicates negatively charged residues, and white indicates uncharged residues.
Figure 7:
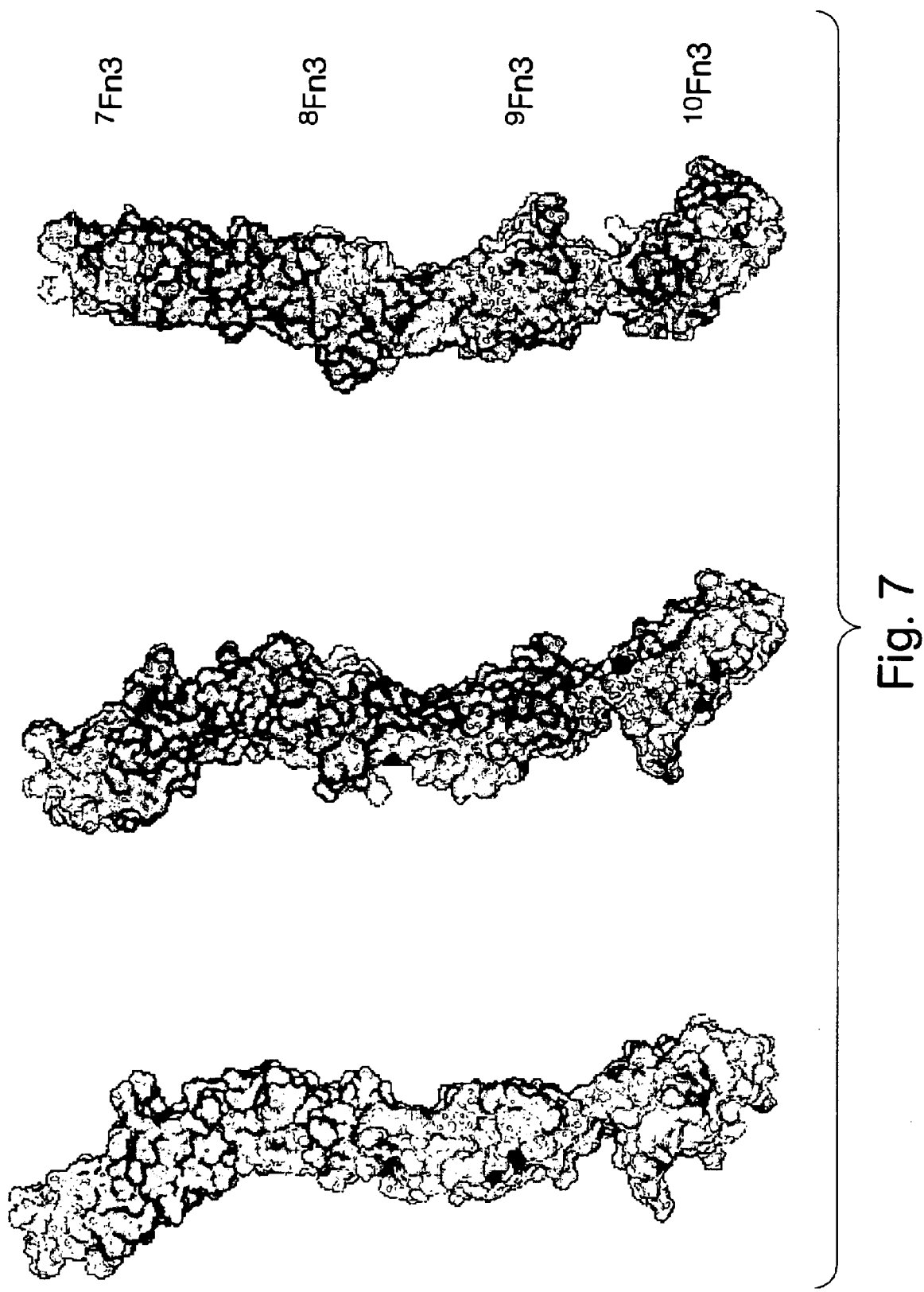
FIG. 7 is a photograph showing space filling models of fibronectin III modules 7–10, in each of three different orientiations. The four modules are labeled. In this figure, blue indicates positively charged residues, red indicates negatively charged residues, and white indicates uncharged residues.

In addition, we have determined that the $^{10}$Fn3 framework possesses exposed loop sequences tolerant of randomization, facilitating the generation of diverse pools of antibody mimics. This determination was made by examining the flexibility of the $^{10}$Fn3 sequence. In particular, the human $^{10}$F3 sequence was aligned with the sequences of fibronectins from other sources as well as sequences of related proteins (FIG. 4), and the results of this alignment were mapped onto the three-dimensional structure of the human $^{10}$Fn3 domain (FIG. 5). This alignment revealed that the majority of conserved residues are found in the core of the beta sheet sandwich, whereas the highly variable residues are located along the edges of the beta sheets, including the N- and C-termini, on the solvent-accessible faces of both beta sheets, and on three solvent-accessible loops that serve as the hypervariable loops for affinity maturation of the antibody mimics. In view of these results, the randomization of these three loops are unlikely to have an adverse effect on the overall fold or stability of the $^{10}$Fn3 framework itself.

For the human $^{10}$Fn3 sequence, this analysis indicates that, at a minimum, amino acids 1–9, 44–50, 61–54, 82–94 (edges of beta sheets); 19, 21, 30–46 (even), 79–65 (odd) (solvent-accessible faces of both beta sheets); 21–31, 51–56, 76–88 (CDR-like solvent-accessible loops); and 14≧16 and 36–45 (other solvent-accessible loops and beta turns) may be randomized to evolve new or improved compound-binding proteins. In addition, as discussed above, alterations in the lengths of one or more solvent exposed loops may also be included in such directed evolution methods. Alternatively, changes in the β-sheet sequences may also be used to evolve new proteins. These mutations change the scaffold and thereby indirectly alter loop structure(s). If this approach is taken, mutations should not saturate the sequence, but rather few mutations should be introduced. Preferably, no more than 10 amino acid changes, and, more preferably, no more than 3 amino acid changes should be introduced to the β-sheet sequences by this approach.

Fibronectin Fusions

The antibody mimics described herein may be fused to other protein domains. For example, these mimics may be integrated with the human immune response by fusing the constant region of an IgG ($F_c$) with a $^{10}$Fn3 module, preferably through the C-terminus of $^{10}$Fn3. The $F_c$ in such a $^{10}$Fn3-$F_c$ fusion molecule activates the complement component of the immune response and increases the therapeutic value of the antibody mimic. Similarly, a fusion between $^{10}$Fn3 and a complement protein, such as C1q, may be used to target cells, and a fusion between $^{10}$Fn3 and a toxin may be used to specifically destroy cells that carry a particular antigen. In addition, $^{10}$Fn3 in any form may be fused with albumin to increase its half-life in the bloodstream and its tissue penetration. Any of these fusions may be generated by standard techniques, for example, by expression of the fusion protein from a recombinant fusion gene constructed using publically available gene sequences.

Fibronectin Scaffold Multimers

In addition to fibronectin monomers, any of the fibronectin constructs described herein may be generated as dimers or multimers of $^{10}$Fn3-based antibody mimics as a means to increase the valency and thus the avidity of antigen binding. Such multimers may be generated through covalent binding between individual $^{10}$Fn3 modules, for example, by imitating the natural $^8$Fn3-$^9$Fn3-$^{10}$Fn3 C-to-N-terminus binding or by imitating antibody dimers that are held together through their constant regions. A $^{10}$Fn3-Fc construct may be exploited to design dimers of the general scheme of $^{10}$Fn3-Fc::Fc-$^{10}$Fn3. The bonds engineered into the Fc::Fc interface may be covalent or non-covalent. In addition, dimerizing or multimerizing partners other than Fc can be used in $^{10}$Fn3 hybrids to create such higher order structures.

In particular examples, covalently bonded multimers may be generated by constructing fusion genes that encode the multimer or, alternatively, by engineering codons for cysteine residues into monomer sequences and allowing disulfide bond formation to occur between the expression products. Non-covalently bonded multimers may also be generated by a variety of techniques. These include the introduction, into monomer sequences, of codons corresponding to positively and/or negatively charged residues and allowing interactions between these residues in the expression products (and therefore between the monomers) to occur. This approach may be simplified by taking advantage of charged residues naturally present in a monomer subunit, for example, the negatively charged residues of fibronectin. Another means for generating non-covalently bonded antibody mimics is to introduce, into the monomer gene (for example, at the amino- or carboxy-termini), the coding sequences for proteins or protein domains known to interact. Such proteins or protein domains include coil-coil motifs, leucine zipper motifs, and any of the numerous protein subunits (or fragments thereof) known to direct formation of dimers or higher order multimers.

Fibronectin-Like Molecules

Although $^{10}$Fn3 represents a preferred scaffold for the generation of antibody mimics, other molecules may be substituted for $^{10}$F3 in the molecules described herein. These include, without limitation, human fibronectin modules $^1$Fn3-$^9$Fn3 and $^{11}$Fn3-$^{17}$Fn3 as well as related Fn3 modules from non-human animals and prokaryotes. In addition, Fn3 modules from other proteins with sequence homology to $^{10}$Fn3, such as tenascins and undulins, may also be used. Modules from different organisms and parent proteins may be most appropriate for different applications; for example, in designing an antibody mimic, it may be most desirable to generate that protein from a fibronectin or fibronectin-like molecule native to the organism for which a therapeutic or diagnostic molecule is intended.

Directed Evolution of Scaffold-Based Binding Proteins

The antibody mimics described herein may be used in any technique for evolving new or improved binding proteins. In one particular example, the target of binding is immobilized on a solid support, such as a column resin or microtiter plate well, and the target contacted with a library of candidate scaffold-based binding proteins. Such a library may consist of $^{10}$Fn3 clones constructed from the wild type $^{10}$Fn3 scaffold through randomization of the sequence and/or the length of the $^{10}$Fn3 CDR-like loops. If desired, this library may be an RNA-protein fusion library generated, for example, by the techniques described in Szostak et al., U.S. Ser. No. 09/007,005, now U.S. Pat. No. 6,258,558 B1, and U.S. Ser. No. 09/247,190, now U.S. Pat. No. 6,261,804 B1; Szostak et al., WO98/31700; and Roberts & Szostak, Proc. Natl. Acad. Sci. USA (1997) vol. 94, p. 12297–12302.

Alternatively, it may be a DNA-protein library (for example, as described in Lohse, DNA-Protein Fusions and Uses Thereof, U.S. Ser. No. 60/110,549, filed Dec. 2, 1998, now abandoned, and U.S. Ser. No. 09/453,190, filed Dec. 2, 1999). The fusion library is incubated with the immobilized target, the support is washed to remove non-specific binders, and the tightest binders are eluted under very stringent conditions and subjected to PCR to recover the sequence information or to create a new library of binders which may be used to repeat the selection process, with or without further mutagenesis of the sequence. A number of rounds of selection may be performed until binders of sufficient affinity for the antigen are obtained.

In one particular example, the $^{10}$Fn3 scaffold may be used as the selection target. For example, if a protein is required that binds a specific peptide sequence presented in a ten residue loop, a single $^{10}$Fn3 clone is constructed in which one of its loops has been set to the length of ten and to the desired sequence. The new clone is expressed in vivo and purified, and then immobilized on a solid support. An RNA-protein fusion library based on an appropriate scaffold is then allowed to interact with the support, which is then washed, and desired molecules eluted and re-selected as described above.

Similarly, the $^{10}$Fn3 scaffold may be used to find natural proteins that interact with the peptide sequence displayed in a $^{10}$Fn3 loop. The $^{10}$Fn3 protein is immobilized as described above, and an RNA-protein fusion library is screened for binders to the displayed loop. The binders are enriched through multiple rounds of selection and identified by DNA sequencing.

In addition, in the above approaches, although RNA-protein libraries represent exemplary libraries for directed evolution, any type of scaffold-based library may be used in the selection methods of the invention.

Use

The antibody mimics described herein may be evolved to bind any antigen of interest. These proteins have thermodynamic properties superior to those of natural antibodies and can be evolved rapidly in vitro. Accordingly, these antibody mimics may be employed in place of antibodies in all areas in which antibodies are used, including in the research, therapeutic, and diagnostic fields. In addition, because these scaffolds possess solubility and stability properties superior to antibodies, the antibody mimics described herein may also be used under conditions which would destroy or inactivate antibody molecules. Finally, because the scaffolds of the present invention may be evolved to bind virtually any compound, these molecules provide completely novel binding proteins which also find use in the research, diagnostic, and therapeutic areas.

Experimental Results

Exemplary scaffold molecules described above were generated and tested, for example, in selection protocols, as follows.

Library Construction

A complex library was constructed from three DNA fragments, each of which contained one randomized area corresponding to a segment encoding a CDR-like loop. The fragments were named BC, DE, and FG, based on the names of the CDR-H-like loops encoded by them; in addition to encoding $^{10}$Fn3 sequence and a randomized sequence, each of the fragments contained stretches encoding an N-terminal His$_6$ domain or a C-terminal FLAG peptide tag. At each junction between two fragments (i.e., between the BC and DE fragments or between the DE and FG fragments), each DNA fragment contained recognition sequences for the Earl Type IIS restriction endonuclease. This restriction enzyme allowed the splicing together of adjacent fragments while removing all foreign, non-$^{10}$Fn3-encoding, sequences. It also allows for a recombination-like mixing of the three $^{10}$Fn3-encoding fragments between cycles of mutagenesis and selection.

Each DNA fragment was assembled from two overlapping oligonucleotides, which were first annealed, then extended to form the double-stranded DNA form of the fragment The oligonucleotides that were used to construct and process the three fragments are listed below; the "Top" and "Bottom" species for each fragment are the oligonucleotides that contained the entire $^{10}$Fn3 encoding sequence. In these oligonucleotides designations, "N" indicates A, T, C, or G; and "S" indicates C or G.

HFnLBCTop(His):
5'-GG AAT TCC TAA TAC GAC TCA CTA TAG GGA CAA TTA CTA TTT ACA ATT ACA ATG CAT CAC CAT CAC CAT CAC GTT TCT GAT GTT CCG AGG GAC CTG GAA GTT GTT GCT GCG ACC CCC ACC AGC-3' (SEQ ID NO: 1)

HfnLBCTop (an alternative N-terminus):
5'-GG AAT TCC TAA TAC GAC TCA CTA TAG GGA CAA TTA CTA TTT ACA ATT ACA ATG GTT TCT GAT GTT CCG AGG GAC CTG GAA GTT GTT GCT GCG ACC CCC ACC AGC-3' (SEQ ID NO: 2)

HFnLBCBot-flag8:
5'-AGC GGA TGC CTT GTC GTC GTC GTC CTT GTA GTC GCT CTT CCC TGT TTC TCC GTA AGT GAT CCT GTA ATA TCT (SNN)7 CCA GCT GAT CAG TAG GCT GGT GGG GGT CGC AGC-3' (SEQ ID NO: 3)

HFnBC3'-flag8:
5'-AGC GGA TGC CTT GTC GTC GTC GTC CTT GTA GTC GCT CTT CCC TGT TTC TCC GTA AGT GAT CC-3' (SEQ ID NO: 4)

HFnLDETop:
5'-GG AAT TCC TAA TAC GAC TCA CTA TAG GGA CAA TTA CTA TTT ACA ATT ACA ATG CAT CAC CAT CAC CAT CAC CTC TTC ACA GGA GGA AAT AGC CCT GTC C-3' (SEQ ID NO: 5)

HFnLDEBot-flag8:
5'-AGC GGA TGC CTT GTC GTC GTC GTC CTT GTA GTC GCT CTT CGT ATA ATC AAC TCC AGG TTT AAG GCC GCT GAT GGT AGC TGT (SNN)4 AGG CAC AGT GAA CTC CTG GAC AGG GCT ATT TCC TCC TGT-3' (SEQ ID NO: 6)

HFnDE3'-flag8:
5'-AGC GGA TGC CTT GTC GTC GTC GTC CTT GTA GTC GCT CTT CGT ATA ATC AAC TCC AGG TTT AAG G-3' (SEQ ID NO: 7)

HFnLFGTop:
5'-GG AAT TCC TAA TAC GAC TCA CTA TAG GGA CAA TTA CTA TTT ACA ATT ACA ATG CAT CAC CAT CAC CAT CAC CTC TTC TAT ACC ATC ACT GTG TAT GCT GTC-3' (SEQ ID NO: 8)

HFnLFGBot-flag8:
5'-AGC GGA TGC CTT GTC GTC GTC GTC CTT GTA GTC TGT TCG GTA ATT AAT GGA AAT TGG (SNN)10 AGT GAC AGC ATA CAC AGT GAT GGT ATA-3' (SEQ ID NO: 9)

HFnFG3'-flag8:
  5'-AGC GGA TGC CTT GTC GTC GTC GTC CTT GTA GTC TGT TCG GTA ATT AAT GGA AAT TGG-3' (SEQ ID NO: 10)

T7TMV (introduces T7 promoter and TMV untranslated region needed for in vitro translation):
  5'-GCG TAA TAC GAC TCA CTA TAG GGA CAA TTA CTA TTT ACA ATT ACA-3' (SEQ ID NO: 11)

ASAflag8:
  5'-AGC GGA TGC CTT GTC GTC GTC GTC CTT GTA GTC-3' (SEQ ID NO: 12)

Unispl-s (splint oligonucleotide used to ligate mRNA to the puromycin-containing linker, described by Roberts et al, 1997, supra): 5'TTTTTTTTTNAGCGGATGC-3' (SEQ ID NO: 13)

A18- - - 2PEG (DNA-puromycin linker):
  5'-(A)18(PEG)2CCPur (SEQ ID NO: 14)

The pairs of oligonucleotides (500 pmol of each) were annealed in 100 µL of 10 mM Tris 7.5, 50 mM NaCl for 10 minutes at 85° C., followed by a slow (0.5–1 hour) cooling to room temperature. The annealed fragments with single-stranded overhangs were then extended using 100 U Klenow (New England Biolabs, Beverly, Mass.) for each 100 µL aliquot of annealed oligos, and the buffer made of 838.5 µl $H_2O$, 9 µl 1M Tris 7.5, 5 µl 1M $MgCl_2$, 20 µl 10 mM dNTPs, and 7.5 µl 1M DTT. The extension reactions proceeded for 1 hour at 25° C.

Next, each of the double-standed DNA fragments was transformed into an RNA-protein fusion using the technique developed by Szostak et al., U.S. Ser. No. 09/007,005 now U.S. Pat. No. 6,258,558 B1 and U.S. Ser. No. 09/247,190 now U.S. Pat. No. 6,261,804 B1; Szostak et al., WO98/31700; and Roberts & Szostak, Proc. Natl. Acad. Sci. USA (1997) vol. 94, p. 12297–12302. Briefly, the fragments were transcribed using an Ambion in vitro transcription kit, MEGAshortscript (Ambion, Austin, Tex.), and the resulting mRNA was gel-purified and ligated to a DNA-puromycin linker using DNA ligase. The mRNA-DNA-puromycin molecule was then translated using the Ambion rabbit reticulocyte lysate-based translation kit. The resulting mRNA-DNA-puromycin-protein fusion was purified using Oligo (dT) cellulose, and a complementary DNA strand was synthesized using reverse transcriptase and the RT primers described above (Unisplint-S or flagASA), following the manufacturer's instructions.

The RNA-protein fusion obtained for each fragment was next purified on the resin appropriate to its peptide purification tag, i.e., on Ni—NTA agarose for the $His_6$-tag and M2 agarose for the FLAG-tag, following the procedure recommended by the manufacturer. The cDNA component of the tag-binding RNA-protein fusions was amplified by PCR using Pharmacia Ready-to-Go PCR Beads, 10 pmol of 5' and 3' PCR primers, and the following PCR program (Pharmacia, Piscataway, N.J.): Step 1: 95° C. for 3 minutes; Step 2: 95° C. for 30 seconds, 58/62° C. for 30 seconds, 72° C. for 1 minute, 20/25/30 cycles, as required; Step 3: 72° C. for 5 minutes; Step 4: 4° C. until end.

The resulting amplified DNA was cleaved by 5 U Earl (New England Biolabs) per1ug DNA; the reaction took place in T4 DNA Ligase Buffer (New England Biolabs) at 37° C., for 1 hour, and was followed by an incubation at 70° C. for 15 minutes to inactivate Ear I. Equal amounts of the BC, DE, and FG DNA fragments were combined and ligated to form a full-length [10]Fn3 gene with randomized loops. The ligation required 10 U of fresh Earl (New England Biolabs) and 20 U of T4 DNA Ligase (Promega, Madison, Wis.), and took 1 hour at 37° C.

Three different DNA libraries were made in the manner described above. Each contained DNA encoding the form of the FG loop with 10 randomized residues. The DNA encoding the BC and the DE loops of the first library bore the wild type [10]Fn3 sequence; DNA encoding a BC loop with 7 randomized residues and a wild type DE loop made up the second library; and DNA encoding a BC loop with 7 randomized residues and a DE loop with 4 randomized residues made up the third library. The complexity of the DNA encoding the FG loop in each of these three libraries was $10^{13}$; the further two randomized loops provided the potential for a complexity too large to be sampled in a laboratory.

Figure 8:
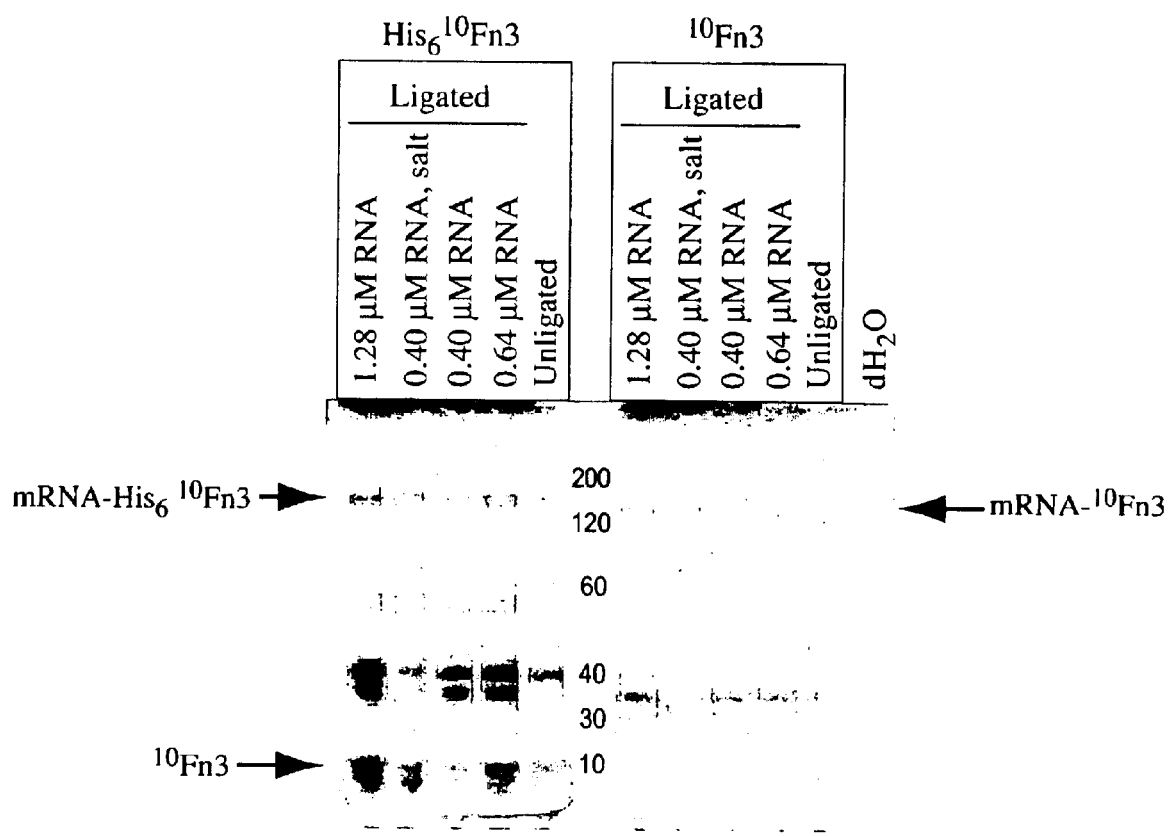
FIG. 8 is a photograph illustrating the formation, under different salt conditions, of RNA-protein fusions which include fibronectin type III domains.

The three DNA libraries constructed were combined into one master library in order to simplify the selection process; target binding itself was expected to select the most suitable library for a particular challenge. RNA-protein fuisions were obtained from the master DNA library following the general procedure described in Szostak et al., U.S. Ser. No. 09/007, 005, now U.S. Pat. No. 6,258,558 B1, and 09/247,190, now U.S. Pat. No. 6,261,804 B1; Szostak et al., WO98/31700; and Roberts & Szostak, Proc. Natl. Acad. Sci. USA (1997) vol. 94, p. 12297–12302 (FIG. 8).

Fusion Selections

The master library in the RNA-protein fusion form was subjected to selection for binding to TNF-α. Two protocols were employed: one in which the target was immobilized on an agarose column and one in which the target was immobilized on a BIACORE chip. First, an extensive optimization of conditions to minimize background binders to the agarose column yielded the favorable buffer conditions of 50 mM HEPES pH 7.4, 0.02% Triton, 100 µg/ml Sheared Salmon Sperm DNA. In this buffer, the non-specific binding of the [10]Fn3 RNA-protein fusion to TNF-α Sepharose was 0.3%. The non-specific binding background of the [10]Fn3 RNA-protein fusion to TNF-α Sepharose was found to be 0.1%.

During each round of selection on TNF-α Sepharose, the RNA-protein fusion library was first preincubated for an hour with underivatized Sepharose to remove any remaining non-specific binders; the flow-through from this pre-clearing was incubated for another hour with TNF-α Sepharose. The TNF-α Sepharose was washed for 3–30 minutes.

Figure 9:
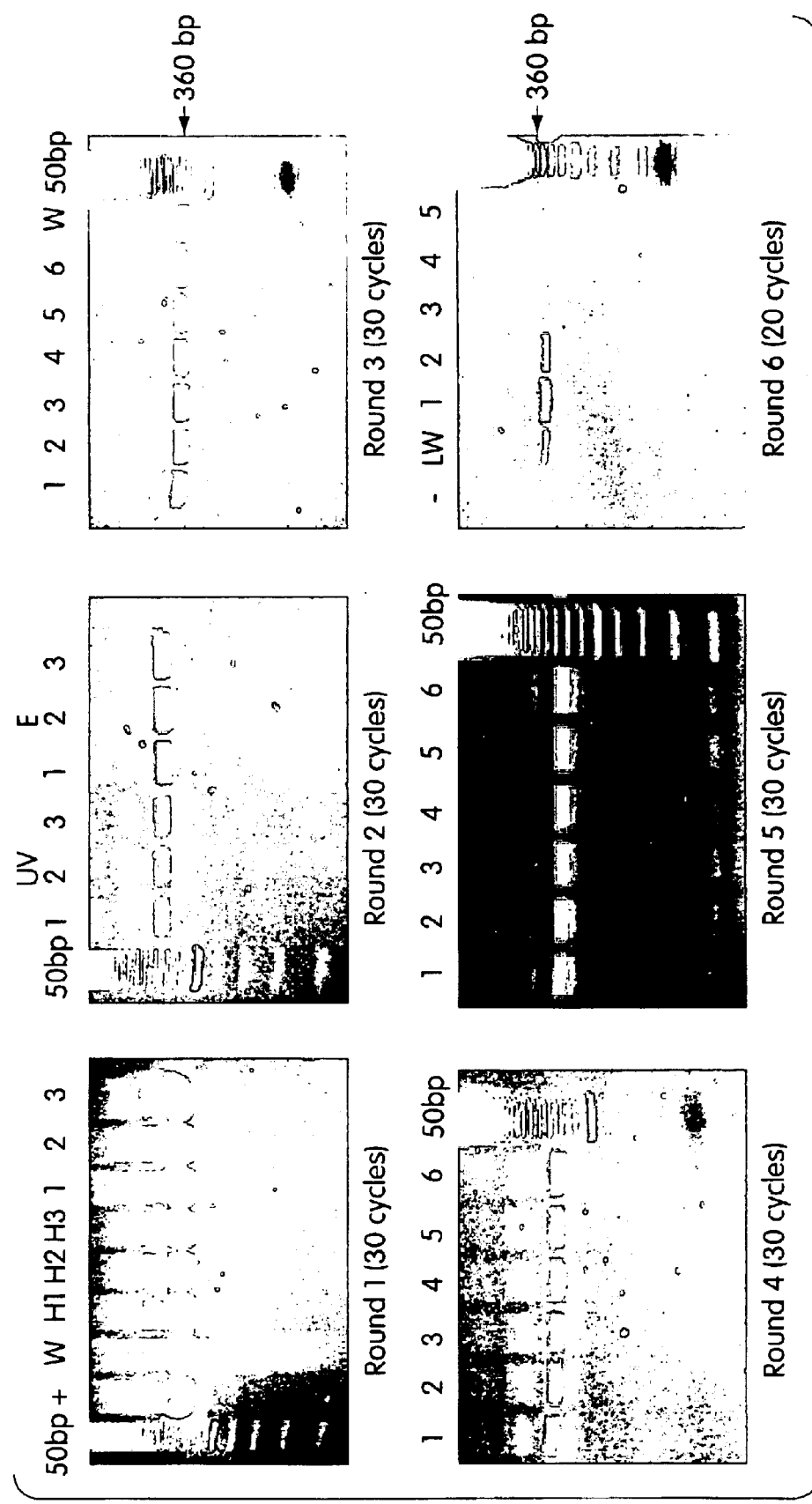
FIG. 9 is a series of photographs illustrating the selection of fibronectin type III domain-containing RNA-protein fusions, as measured by PCR signal analysis.

After each selection, the cDNA from the RNA-protein fusion that had been eluted from the solid support with 0.3M NaOH or 0.1M KOH was amplified by PCR; a DNA band of the expected size persisted through multiple rounds of selection (FIG. 9); similar results were observed in the two alternative selection protocols, and only the data from the agarose column selection is shown in FIG. 9.

Figure 10:
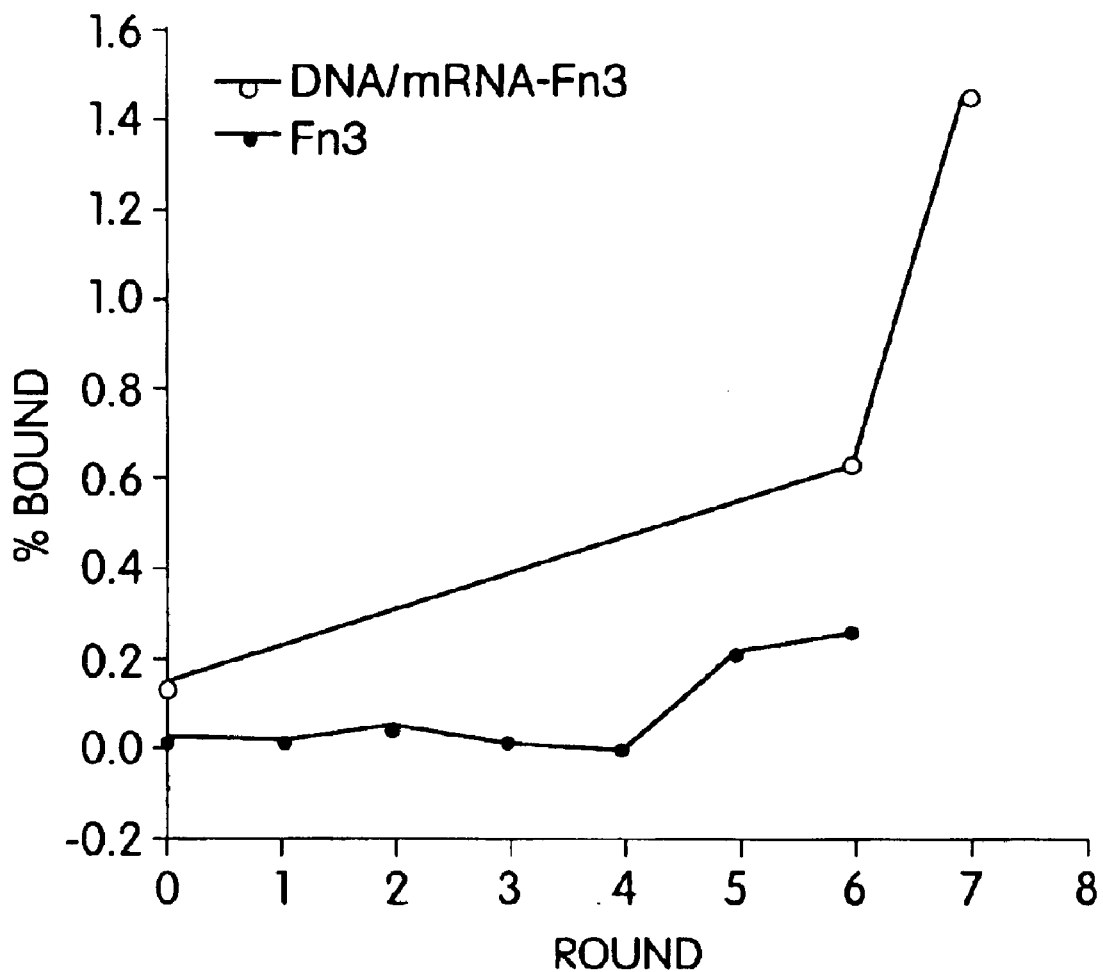
FIG. 10 is a graph illustrating an increase in the percent TNF-α binding during the selections described herein, as well as a comparison between RNA-protein fusion and free protein selections.

In the first seven rounds, the binding of library RNA-protein fusions to the target remained low; in contrast, when free protein was translated from DNA pools at different stages of the selection, the proportion of the column binding species increased significantly between rounds (FIG. 10). Similar selections may be carried out with any other binding species target (for example, IL-1 and IL-13).

Animal Studies

Wild-type [10]Fn3 contains an integrin-binding tripeptide motif, Arginine 78-Glycine 79-Aspartate 80 (the "RGD motif) at the tip of the FG loop. In order to avoid integrin binding and a potential inflammatory response based on this tripeptide in vivo, a mutant form of [10]Fn3 was generated that contained an inert sequence, Serine 78-Glycine 79-Glutamate 80 (the "SGE mutant"), a sequence which is found in the closely related, wild-type $^{11}$Fn3 domain. This SGE mutant was expressed as an N-terminally His$_6$-tagged, free protein in *E. coli*, and purified to homogeneity on a metal chelate column followed by a size exclusion column.

In particular, the DNA sequence encoding His$_6$-$^{10}$Fn3 (SGE) was cloned into the pET9a expression vector and transformed into BL21 DE3 pLysS cells. The culture was then grown in LB broth containing 50 µg/mL kanamycin at 37° C., with shaking, to $A_{560}$=1.0, and was then induced with 0.4 mM IPTG. The induced culture was further incubated, under the same conditions, overnight (14–18 hours); the bacteria were recovered by standard, low speed centrifugation. The cell pellet was resuspended in 1/50 of the original culture volume of lysis buffer (50 mM Tris 8.0, 0.5 M NaCl, 5% glycerol, 0.05% Triton X-100, and 1 mM PMSF), and the cells were lysed by passing the resulting paste through a Microfluidics Corporation Microfluidizer M110-EH, three times. The lysate was clarified by centrifugation, and the supernatant was filtered through a 0.45 µm filter followed by filtration through a 0.2 µm filter. 100 mL of the clarified lysate was loaded onto a 5 mL Talon cobalt column (Clontech, Palo Alto, Calif.), washed by 70 mL of lysis buffer, and eluted with a linear gradient of 0–30 mM imidazole in lysis buffer. The flow rate through the column through all the steps was 1 mL/min. The eluted protein was concentrated 10-fold by dialysis (MW cutoff= 3,500) against 15,000–20,000 PEG. The resulting sample was dialysed into buffer 1 (lysis buffer without the glycerol), then loaded, 5 mL at a time, onto a 16×60 mm Sephacryl 100 size exclusion column equilibrated in buffer 1. The column was run at 0.8 mL/min, in buffer 1; all fractions that contained a protein of the expected MW were pooled, concentrated 10× as described above, then dialyzed into PBS. Toxikon (MA) was engaged to perform endotoxin screens and animal studies on the resulting sample.

In these animal studies, the endotoxin levels in the samples examined to date have been below the detection level of the assay. In a preliminary toxicology study, this protein was injected into two mice at the estimated 100× therapeutic dose of 2.6 mg/mouse. The animals survived the two weeks of the study with no apparent ill effects. These results suggest that $^{10}$Fn3 may be incorporated safely into an IV drug.

Alternative Constructs for In Vivo Use

Figure 11:
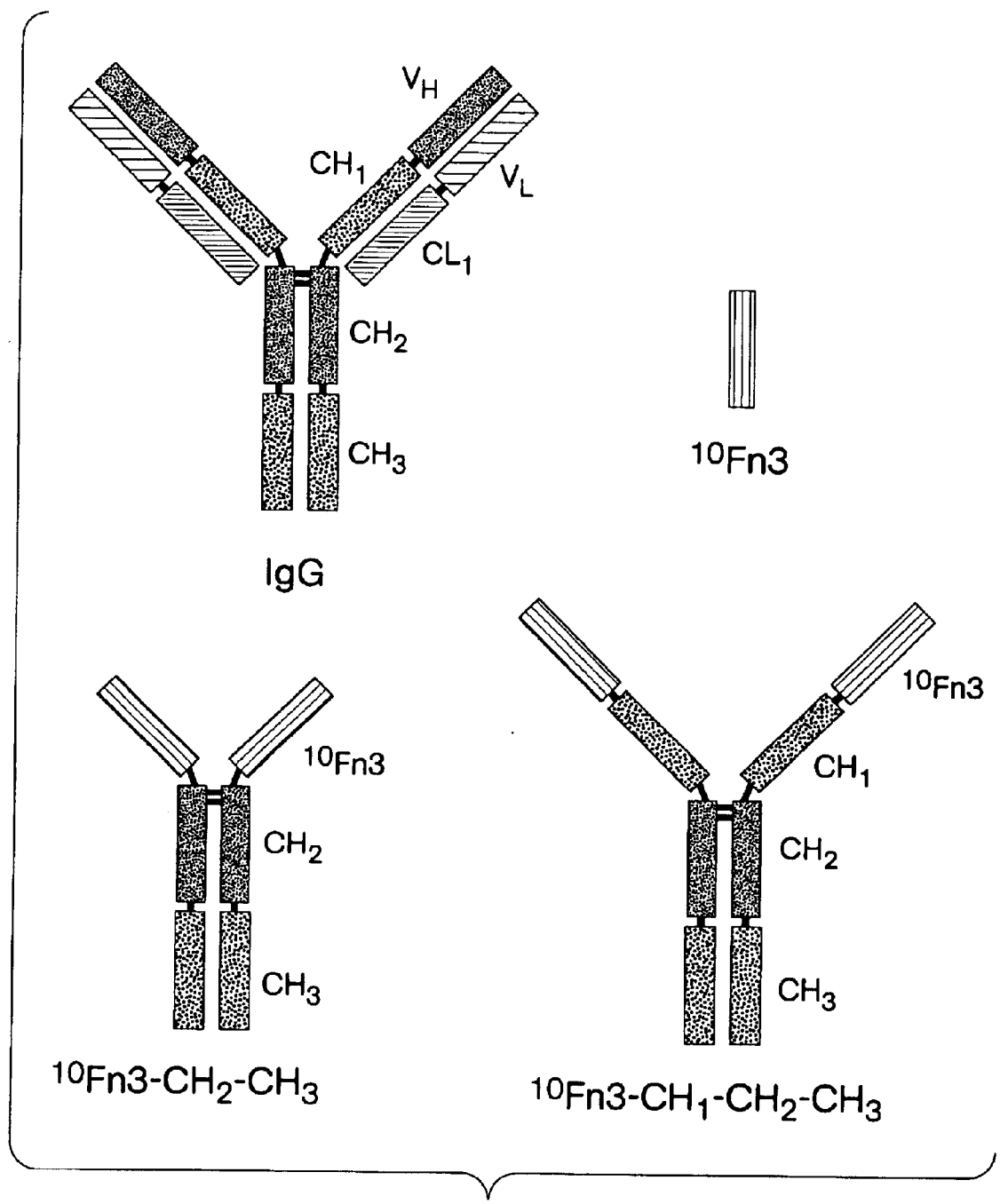
FIG. 11 is a series of schematic representations showing IgG, $^{10}$Fn3, Fn—CH$_1$—CH$_2$—CH$_3$, and Fn—CH$_2$—CH$_3$ (clockwise from top left).
Figure 12:
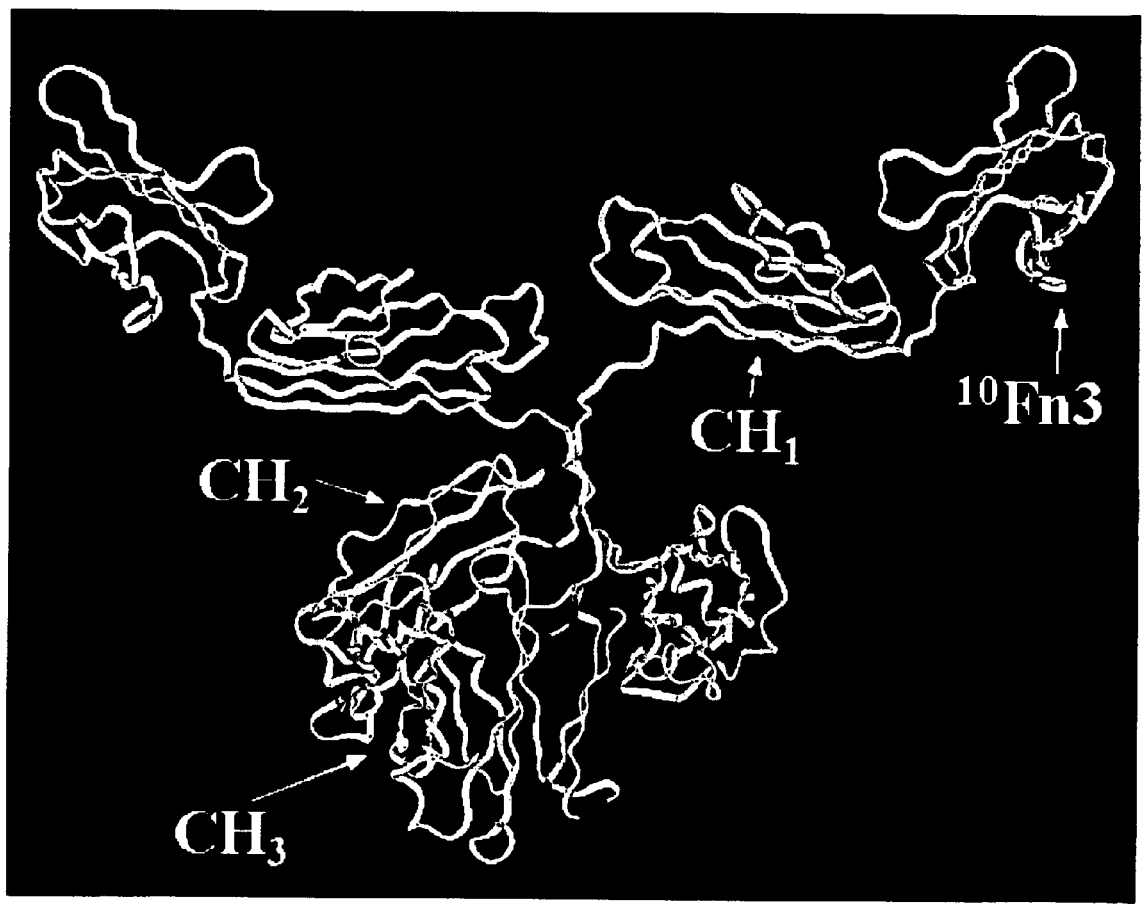
FIG. 12 is a photograph showing a molecular model of Fn—CH$_1$—CH$_2$—CH$_3$ based on known three-dimensional structures of IgG (X-ray crystallography) and $^{10}$Fn3 (NMR and X-ray crystallography).

To extend the half life of the 8 kD $^{10}$Fn3 domain, a larger molecule has also been constructed that mimics natural antibodies. This $^{10}$Fn3-F$_c$ molecule contains the —CH$_1$—CH$_2$—CH$_3$ (FIG. 11) or —CH$_2$—CH$_3$ domains of the IgG constant region of the host; in these constructs, the $^{10}$Fn3 domain is grafted onto the N-terminus in place of the IgG V$_H$ domain (FIGS. 11 and 12). Such antibody-like constructs are expected to improve the pharmacokinetics of the protein as well as its ability to harness the natural immune response.

In order to construct the murine form of the $^{10}$Fn3—CH$_1$—CH$_2$—CH$_3$ clone, the —CH$_1$—CH$_2$—CH$_3$ region was first amplified from a mouse liver spleen cDNA library (Clontech), then ligated into the pET25b vector. The primers used in the cloning were 5' Fc Nest and 3' 5 Fc Nest, and the primers used to graft the appropriate restriction sites onto the ends of the recovered insert were 5' Fc HIII and 3' Fc Nhe:

5' Fc Nest 5'GCG GCA GGG TTT GCT TAC TGG GGC CAA GGG 3' (SEQ ID NO: 15);

3' Fc Nest 5'GGG AGG GGT GGA GGT AGG TCA CAG TCC 3' (SEQ ID NO: 16);

3' Fc Nhe 5' TTT GCT AGC TTT ACC AGG AGA GTG GGA GGC 3' (SEQ ID NO: 17); and

5' Fc HIII 5' AAA AAG CTT GCC AAA ACG ACA CCC CCA TCT GTC 3' (SEQ ID NO: 18).

Further PCR is used to remove the CH$_1$ region from this clone and create the Fc part of the shorter, $^{10}$Fn3—CH$_2$—CH$_3$ clone. The sequence encoding $^{10}$Fn3 is spliced onto the 5' end of each clone; either the wild type $^{10}$Fn3 cloned from the same mouse spleen cDNA library or a modified $^{10}$Fn3 obtained by mutagenesis or randomization of the molecules can be used. The oligonucleotides used in the cloning of murine wild-type $^{10}$Fn3 were:

Mo 5PCR-NdeI: 5' CATATGGTTTCTGATATTC-CGAGAGATCTGGAG 3' (SEQ ID NO: 19);

Mo5PCR-His-NdeI (for an alternative N-terminus with the His$_6$ purification tag): 5' CAT ATG CAT CAC CAT CAC CAT CAC GTT TCT GAT ATT CCG AGA 3' (SEQ ID NO: 20); and Mo3PCR-EcoRI: 5' GAATTCCTATGTTTTATAAT-TGATGGAAAC3' (SEQ ID NO: 21).

The human equivalents of the clones are constructed using the same strategy with human oligonucleotide sequences.

$^{10}$Fn3 Scaffolds in Protein Chip Applications

The suitability of the $^{10}$Fn3 scaffold for protein chip applications is the consequence of (1) its ability to support many binding functions which can be selected rapidly on the bench or in an automated setup, and (2) its superior biophysical properties.

The versatile binding properties of $^{10}$Fn3 are a function of the loops displayed by the Fn3 immunoglobulin-like, beta sandwich fold. As discussed above, these loops are similar to the complementarity determining regions of antibody variable domains and can cooperate in a way similar to those antibody loops in order to bind antigens. In our system, $^{10}$Fn3 loops BC (residues 21–30), DE (residues 51–56), and FG (residues 76–87) are randomized either in sequence, in length, or in both sequence and length in order to generate diverse libraries of mRNA-$^{10}$Fn3 fusions. The binders in such libraries are then enriched based on their affinity for an immobilized or tagged target, until a small population of high affinity binders are generated. Also, error-prone PCR and recombination can be employed to facilitate affinity maturation of selected binders. Due to the rapid and efficient selection and affinity maturation protocols, binders to a large number of targets can be selected in a short time.

As a scaffold for binders to be immobilized on protein chips, the $^{10}$Fn3 domain has the advantage over antibody fragments and single-chain antibodies of being smaller and easier to handle. For example, unlike single-chain scaffolds or isolated variable domains of antibodies, which vary widely in their stability and solubility, and which require an oxidizing environment to preserve their structurally essential disulfide bonds, $^{10}$Fn3 is extremely stable, with a melting temperature of 110° C., and solubility at a concentration>16 mg/mL. The $^{10}$Fn3 scaffold also contains no disulfides or free cysteines; consequently, it is insensitive to the redox potential of its environment. A further advantage of $^{10}$Fn3 is that its antigen-binding loops and N-terminus are on the edge of the beta-sandwich opposite to the C-terminus; thus the attachment of a $^{10}$Fn3 scaffold to a chip by its C-terminus aligns the antigen-binding loops, allowing for their greatest accessibility to the solution being assayed. Since $^{10}$Fn3 is a single domain of only 94 amino acid residues, it is also possible to immobilize it onto a chip surface at a higher density than is used for single-chain antibodies, with their approximately 250 residues. In addition, the hydrophilicity of the $^{10}$Fn3 scaffold, which is reflected in the high solubility of this domain, leads to a lower than average background binding of $^{10}$Fn3 to a chip surface.

The stability of the $^{10}$Fn3 scaffold as well as its suitability for library formation and selection of binders are likely to be shared by the large, Fn3-like class of protein domains with an immunoglobulin-like fold, such as the domains of tenascin, N-cadherin, E-cadherin, ICAM, titin, GCSF-R, cytokine receptor, glycosidase inhibitor, and antibiotic chromoprotein. The key features shared by all such domains are a stable framework provided by two beta-sheets, which are packed against each other and which are connected by at least three solvent-accessible loops per edge of the sheet; such loops can be randomized to generate a library of potential binders without disrupting the structure of the framework (as described above).

Immobilization of Fibronectin Scaffold Binders (Fn-binders)

To immobilize Fn-binders to a chip surface, a number of exemplary techniques may be utilized. For example, Fn-binders may be immobilized as RNA-protein fusions by Watson-Crick hybridization of the RNA moiety of the fusion to a base complementary DNA immobilized on the chip surface (as described, for example, in Addressable Protein Arrays, U.S. Ser. No. 60/080,686; U.S. Ser. No. 09/282,734; and WO 99/51773). Alternatively, Fn-binders can be immobilized as free proteins directly on a chip surface. Manual as well as robotic devices may be used for deposition of the Fn-binders on the chip surface. Spotting robots can be used for deposition of Fn-binders with high density in an array format (for example, by the method of Lueking et al., Anal Biochem. 1999 May 15;270(1):103–11). Different methods may also be utilized for anchoring the Fn-binder on the chip surface. A number of standard immobilization procedures may be used including those described in Methods in Enzymology (K. Mosbach and B. Danielsson, eds.), vols. 135 and 136, Academic Press, Orlando, Fla., 1987; Nilsson et al., Protein Expr. Purif. 1997 October; 11(1): 1–16; and references therein. Oriented immobilization of Fn-binders can help to increase the binding capacity of chip-bound Fn-binders. Exemplary approaches for achieving oriented coupling are described in Lu et al., The Analyst (1996), vol. 121, p. 29R–32R; and Turkova, J Chromatogr B Biomed Sci App. 1999 February 5;722(1–2):11–31. In addition, any of the methods described herein for anchoring Fn-binders to chip surfaces can also be applied to the immobilization of Fn-binders on beads, or other supports.

Target Protein Capture and Detection

Selected populations of Fn-binders may be used for detection and/or quantitation of analyte targets, for example, in samples such as biological samples. To carry out this type of diagnostic assay, selected Fn-binders to targets of interest are immobilized on an appropriate support to form multi-featured protein chips. Next, a sample is applied to the chip, and the components of the sample that associate with the Fn-binders are identified based on the target-specificity of the immobilized binders. Using this technique, one or more components may be simultaneously identified or quantitated in a sample (for example, as a means to carry out sample profiling).

Methods for target detection allow measuring the levels of bound protein targets and include, without limitation, radiography, fluorescence scanning, mass spectroscopy (MS), and surface plasmon resonance (SPR). Autoradiography using a phosphorimager system (Molecular Dynamics, Sunnyvale, Calif.) can be used for detection and quantification of target protein which has been radioactively labeled, e.g., using $^{35}$S methionine. Fluorescence scanning using a laser scanner (see below) may be used for detection and quantification of fluorescently labeled targets. Alternatively, fluorescence scanning may be used for the detection of fluorescently labeled ligands which themselves bind to the target protein (e.g., fluorescently labeled target-specific antibodies or fluorescently labeled streptavidin binding to target-biotin, as described below).

Mass spectroscopy can be used to detect and identify bound targets based on their molecular mass. Desorption of bound target protein can be achieved with laser assistance directly from the chip surface as described below. Mass detection also allows determinations, based on molecular mass, of target modifications including post-translational modifications like phosphorylation or glycosylation. Surface plasmon resonance can be used for quantification of bound protein targets where the Fn-binder(s) are immobilized on a suitable gold-surface (for example, as obtained from Biacore, Sweden).

Described below are exemplary schemes for selecting Fn binders (in this case, Fn-binders specific for the protein, TNF-α) and the use of those selected populations for detection on chips. This example is provided for the purpose of illustrating the invention, and should not be construed as limiting.

Selection of TNF-α Binders Based on $^{10}$Fn3 Scaffold

In one exemplary use for fibronectin scaffold selection on chips, a $^{10}$Fn3-scaffold library-based selection was performed against TNF-α, using library of human $^{10}$Fn3 variants with randomized loops BC, DE, and FG. The library was constructed from three DNA fragments, each of which contained nucleotide sequences that encoded approximately one third of human $^{10}$Fn3, including one of the randomized loops. The DNA sequences that encoded the loop residues listed above were rebuilt by oligonucleotide synthesis, so that the codons for the residues of interest were replaced by (NNS)n, where N represents any of the four deoxyribonucleotides (A, C, G, or T), and S represents either C or G. The C-terminus of each fragment contained the sequence for the FLAG purification tag.

Once extended by Klenow, each DNA fragment was transcribed, and the transcript was ligated to a puromycin-containing DNA linker, and translated in vitro, as described by Szostak et al. (Roberts and Szostak Proc. Natl. Acad. Sci USA 94:12297, 1997; Szostak et al., U.S. Ser. No. 09/007,005, now U.S. Pat. No. 6,258,558 B1 and U.S. Ser. No. 09/247,190, now U.S. Pat. No. 6,261,804 B1; Szostak et al., WO98/31700), to generate an mRNA-peptide fusion, which was then reverse-transcribed into a DNA-mRNA-peptide fusion. The binding of the FLAG-tagged peptide to M2 agarose separated full-length fusion molecules from those containing frameshifts or superfluous stop codons; the DNA associated with the purified full-length fusion was amplified by PCR, then the three DNA fragments were cut by Ear I restriction endonuclease and ligated to form the full length template. The template was transcribed, and the transcript was ligated to puromycin-containing DNA linkers, and translated to generate a $^{10}$Fn3-RNA-protein fusion library, which was then reverse-transcribed to yield the DNA-mRNA-peptide fusion library which was subsequently used in the selection.

Selection for TNF-α binders took place in 50 mM HEPES, pH 7.4, 0.02% Triton-X, 0.1 mg/mL salmon sperm DNA. The RNA-protein library was incubated with Sepharose-immobilized TNF-α; after washing, the DNA associated with the tightest binders was eluted with 0.1 M KOH, amplified by PCR, and transcribed, and the transcript ligated, translated, and reverse-transcribed into the starting material for the next round of selection.

Figure 13:
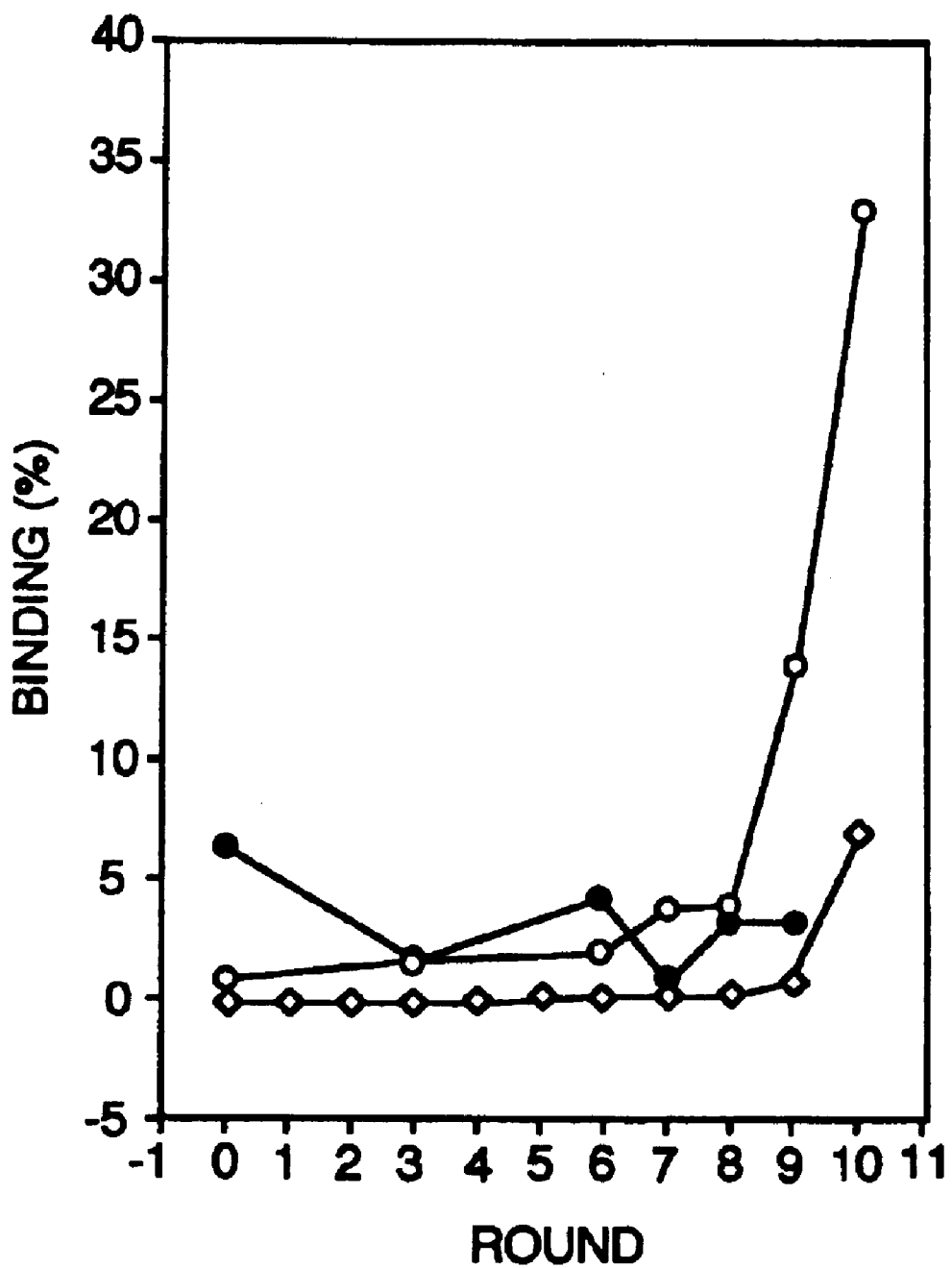
FIG. 13 is a graph showing the time course of an exemplary $^{10}$Fn3-based nucleic acid-protein fusion selection of TNF-α binders. The proportion of nucleic acid-protein fusion pool (open diamonds) and free protein pool (open circles) that bound to TNF-α-Sepharose, and the proportion of free protein pool (full circles) that bound to underivatized Sepharose, are shown.

Ten rounds of such selection were performed (as shown in FIG. 13); they resulted in an RNA-protein fusion pool that bound to TNF-α-Sepharose with the apparent average Kd of 120 nM. Specific clonal components of the pool that were characterized showed TNF-α binding in the range of 50–500 nM.

Fn-binder Immobilization, Target Protein Capture, and MALDI-TOF Detection

As a first step toward immobilizing the Fn-binders to a chip surface, an oligonucleotide capture probe was prepared with an automated DNA synthesizer (PE BioSystems Expedite 8909) using the solid-support phosphoramidite approach. All reagents were obtained from Glen Research. Synthesis was initiated with a solid support containing a disulfide bond to eventually provide a 3'-terminal thiol functionality. The first four monomers to be added were hexaethylene oxide units, followed by 20 T monomers. The 5'-terminal DMT group was not removed. The capture probe was cleaved from the solid support and deprotected with ammonium hydroxide, concentrated to dryness in a vacuum centrifuge, and purified by reverse-phase HPLC using an acetonitrile gradient in triethylammonium acetate buffer. Appropriate fractions from the HPLC were collected, evaporated to dryness in a vacuum centrifuge, and the 5'-terminal DMT group was removed by treatment with 80% AcOH for 30 minutes. The acid was removed by evaporation, and the oligonucleotide was then treated with 100 mM DTT for 30 minutes to cleave the disulfide bond. DTT was removed by repeated extraction with EtOAc. The oligonucleotide was ethanol precipitated from the remaining aqueous layer and checked for purity by reverse-phase HPLC.

The 3'-thiol capture probe was adjusted to 250 μM in degassed 1×PBS buffer and applied as a single droplet (75 μL) to a 9×9 mm gold-coated chip (Biacore) in an argon-flushed chamber containing a small amount of water. After 18 hours at room temperature, the capture probe solution was removed, and the functionalized chip was washed with 50 mL 1×PBS buffer (2× for 15 minutes each) with gentle agitation, and then rinsed with 50 mL water (2× for 15 minutes each) in the same fashion. Remaining liquid was carefully removed and the functionalized chips were either used immediately or stored at 4° C. under argon.

About 1 pmol of $^{10}$Fn3 fusion pool from the Round 10 TNF-α selection (above) was treated with RNAse A for several hours, adjusted to 5×SSC in 70 μL, and applied to a functionalized gold chip from above as a single droplet. A 50 μL volume gasket device was used to seal the fusion mixture with the functionalized chip, and the apparatus was continuously rotated at 4° C. After 18 hours the apparatus was disassembled, and the gold chip was washed with 50 mL 5×SSC for 10 minutes with gentle agitation. Excess liquid was carefully removed from the chip surface, and the chip was passivated with a blocking solution (1×TBS+0.02% Tween-20+0.25% BSA) for 10 minutes at 4° C. Excess liquid was carefully removed, and a solution containing 500 μg/mL TNF-α in the same composition blocking solution was applied to the chip as a single droplet and incubated at 4° C. for two hours with occasional mixing of the droplet via Pipetman. After removal of the binding solution, the chip was washed for 5 minutes at 4° C. with gentle agitation (50 mL 1×TBS+0.02% Tween-20) and then dried at room temperature. A second chip was prepared exactly as described above, except fusion was not added to the hybridization mix.

Next, MALDI-TOF matrix (15 mg/mL 3,5-dimethoxy-4-hydroxycinnamic acid in 1:1 ethanol/10% formic acid in water) was uniformly applied to the gold chips with a high-precision 3-axis robot (MicroGrid, BioRobotics). A 16-pin tool was used to transfer the matrix from a 384-well microtiter plate to the chips, producing 200 micron diameter features with a 600 micron pitch. The MALDI-TOF mass spectrometer (Voyager DE, PerSeptive Biosystems) instrument settings were as follows: Accelerating Voltage=25k, Grid Voltage=92%, Guide Wire Voltage=0.05%, Delay=200 on, Laser Power=2400, Low Mass Gate=1500, Negative Ions=off. The gold chips were individually placed on a MALDI sample stage modified to keep the level of the chip the same as the level of the stage, thus allowing proper flight distance. The instrument's video monitor and motion control system were used to direct the laser beam to individual matrix features.

Figure 14:
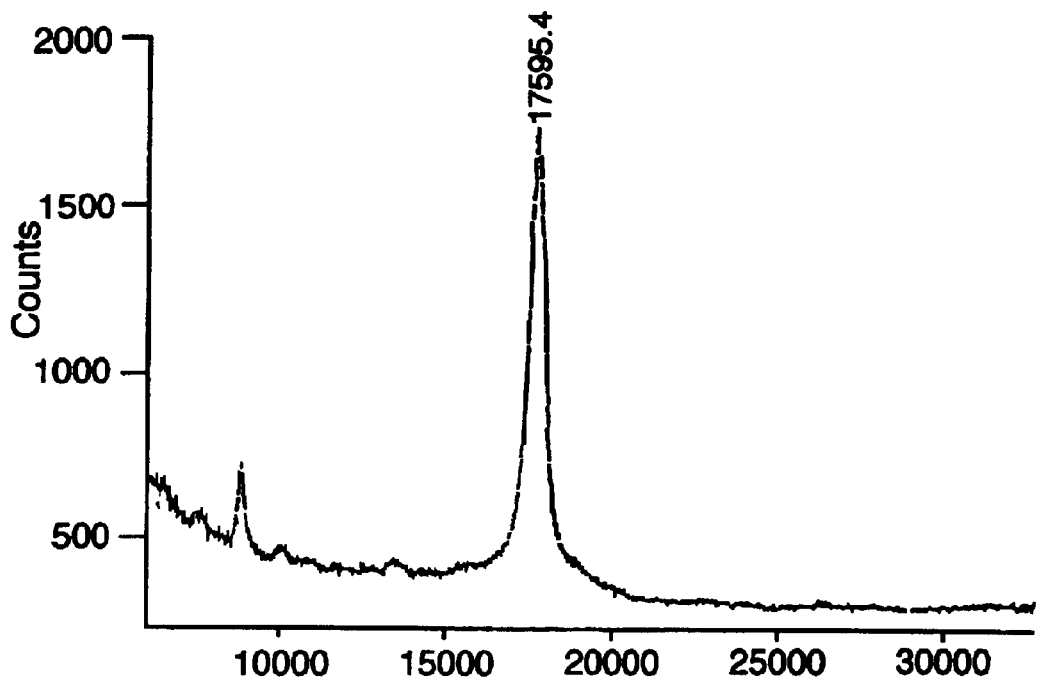
FIGS. 14 and 15 are graphs illustrating TNF-α binding by TNF-α Fn-binders. In particular, these figures show mass spectra data obtained from a $^{10}$Fn3 fusion chip and non-fusion chip, respectively.
Figure 15:
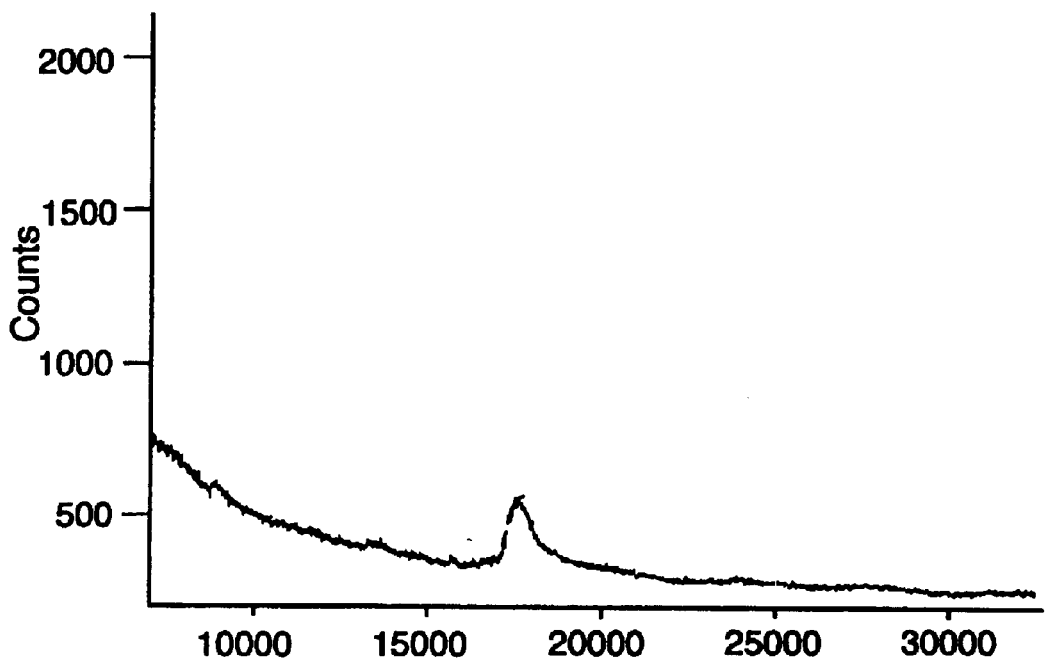

FIGS. 14 and 15 show the mass spectra from the $^{10}$Fn3 fusion chip and the non-fusion chip, respectively. In each case, a small number of 200 micron features were analyzed to collect the spectra, but FIG. 15 required significantly more acquisitions. The signal at 17.5 kDa corresponds to TNF-α monomer.

Fn-binder Immobilization, Target Protein Capture, and Fluorescence Detection Pre-cleaned 1×3 inch glass microscope slides (Goldseal, #3010) were treated with Nanostrip (Cyantek) for 15 minutes, 10% aqueous NaOH at 70° C. for 3 minutes, and 1% aqueous HCl for 1 minute, thoroughly rinsing with deionized water after each reagent. The slides were then dried in a vacuum desiccator over anhydrous calcium sulfate for several hours. A 1% solution of aminopropyltrimethoxysilane in 95% acetone/5% water was prepared and allowed to hydrolyze for 20 minutes. The glass slides were immersed in the hydrolyzed silane solution for 5 minutes with gentle agitation. Excess silane was removed by subjecting the slides to ten 5-minute washes, using fresh portions of 95% acetone/5% water for each wash, with gentle agitation. The slides were then cured by heating at 110° C. for 20 minutes. The silane treated slides were immersed in a freshly prepared 0.2% solution of phenylene 1,4-diisothiocyanate in 90% DMF/10% pyridine for two hours, with gentle agitation. The slides were washed sequentially with 90% DMF/10% pyridine, methanol, and acetone. After air drying, the functionalized slides were stored at 0° C. in a vacuum desiccator over anhydrous calcium sulfate. Similar results were obtained with commercial amine-reactive slides (3-D Link, Surmodics).

Oligonucleotide capture probes were prepared with an automated DNA synthesizer (PE BioSystems Expedite 8909) using conventional phosphoramidite chemistry. All reagents were from Glen Research. Synthesis was initiated with a solid support bearing an orthogonally protected amino functionality, whereby the 3'-terminal amine is not unmasked until final deprotection step. The first four monomers to be added were hexaethylene oxide units, followed by the standard A, G, C and T monomers. All capture oligo sequences were cleaved from the solid support and deprotected with ammonium hydroxide, concentrated to dryness, precipitated in ethanol, and purified by reverse-phase HPLC using an acetonitrile gradient in triethylammonium acetate buffer. Appropriate fractions from the HPLC were collected, evaporated to dryness in a vacuum centrifuge, and then coevaporated with a portion of water.

The purified, amine-labeled capture oligos were adjusted to a concentration of 250 µM in 50 mM sodium carbonate buffer (pH 9.0) containing 10% glycerol. The probes were spotted onto the amine-reactive glass surface at defined positions in a 5×5×6 array pattern with a 3-axis robot (MicroGrid, BioRobotics). A 16-pin tool was used to transfer the liquid from 384-well microtiter plates, producing 200 micron features with a 600 micron pitch. Each sub-grid of 24 features represents a single capture probe (i.e., 24 duplicate spots). The arrays were incubated at room temperature in a moisture-saturated environment for 12–18 hours. The attachment reaction was terminated by immersing the chips in 2% aqueous ammonium hydroxide for five minutes with gentle agitation, followed by rinsing with distilled water (3× for 5 minutes each). The array was finally soaked in 10×PBS solution for 30 minutes at room temperature, and then rinsed again for 5 minutes in distilled water.

Specific and thermodynamically isoenergetic sequences along the $^{10}$Fn3 mRNA were identified to serve as capture points to self-assemble and anchor the $^{10}$Fn3 protein. The software program HybSimulator v4.0 (Advanced Gene Computing Technology, Inc.) facilitated the identification and analysis of potential capture probes. Six unique capture probes were chosen and printed onto the chip, three of which are complementary to common regions of the $^{10}$Fn3 fusion pool's mRNA (CP3', CP5', and CPflag). The remaining three sequences (CPneg1, CPneg2, and CPneg3) are not complementary and function in part as negative controls. Each of the capture probes possesses a 3'-amino terminus and four hexaethylene oxide spacer units, as described above. The following is a list of the capture probe sequences that were employed (5'→3'):

CP3': TGTAAATAGTAATTGTCCC (SEQ ID NO: 22)
CP5': TTTTTTTTTTTTTTTTTTTT (SEQ ID NO: 23)
CPneg1: CCTGTAGGTGTCCAT (SEQ ID NO: 24)
CPflag: CATCGTCCTTGTAGTC (SEQ ID NO: 25)
CPneg2: CGTCGTAGGGGTA (SEQ ID NO: 26)
CPneg3: CAGGTCTTCTTCAGAGA (SEQ ID NO: 27)

About 1 pmol of $^{10}$Fn3 fusion pool from the Round 10 TNF-α selection was adjusted to 5×SSC containing 0.02% Tween-20 and 2 mM vanadyl ribonucleotide complex in a total volume of 350 µL. The entire volume was applied to the microarray under a 400 µL gasket device and the assembly was continuously rotated for 18 hours at room temperature. After hybridization the slide was washed sequentially with stirred 500 mL portions of 5×SSC, 2.5×SSC, and 1×SSC for 5 minutes each. Traces of liquid were removed by centrifugation and the slide was allowed to air-dry.

Recombinant human TNF-α (500 µg, lyophilized, from PreproTech) was taken up in 230 µL 1×PBS and dialyzed against 700 mL stirred 1×PBS at 4° C. for 18 hours in a Microdialyzer unit (3,500 MWCO, Pierce). The dialyzed TNF-α was treated with EZ-Link NHS-LC-LC biotinylation reagent (20 µg, Pierce) for 2 hours at 0° C., and again dialyzed against 700 mL stirred 1×PBS at 4° C. for 18 hours in a Microdialyzer unit (3,500 MWCO, Pierce). The resulting conjugate was analyzed by MALDI-TOF mass spectrometry and was found to be almost completely functionalized with a single biotin moiety.

Each of the following processes was conducted at 4° C. with continuous rotation or mixing. The protein microarray surface was passivated by treatment with 1×TBS containing 0.02% Tween-20 and 0.2% BSA (200 µL) for 60 minutes. Biotinylated TNF-α (100 nM concentration made up in the passivation buffer) was contacted with the microarray for 120 minutes. The microarray was washed with 1×TBS containing 0.02% Tween-20 (3×50 mL, 5 minutes each wash). Fluorescently labeled streptavidin (2.5 µg/mL Alexa 546-streptavidin conjugate from Molecular Probes, made up in the passivation buffer) was contacted with the microarray for 60 minutes. The microarray was washed with 1×TBS containing 0.02% Tween-20 (2×50 mL, 5 minutes each wash) followed by a 3 minute rinse with 1×TBS. Traces of liquid were removed by centrifugation, and the slide was allowed to air-dry at room temperature.

Fluorescence laser scanning was performed with a GSI Lumonics ScanArray 5000 system using 10 µM pixel resolution and preset excitation and emission wavelengths for Alexa 546 dye. Phosphorimage analysis was performed with a Molecular Dynamics Storm system. Exposure time was 48 hours with direct contact between the microarray and the phosphor storage screen. Phosphorimage scanning was performed at the 50 µM resolution setting, and data was extracted with ImageQuant v.4.3 software.

Figure 16:
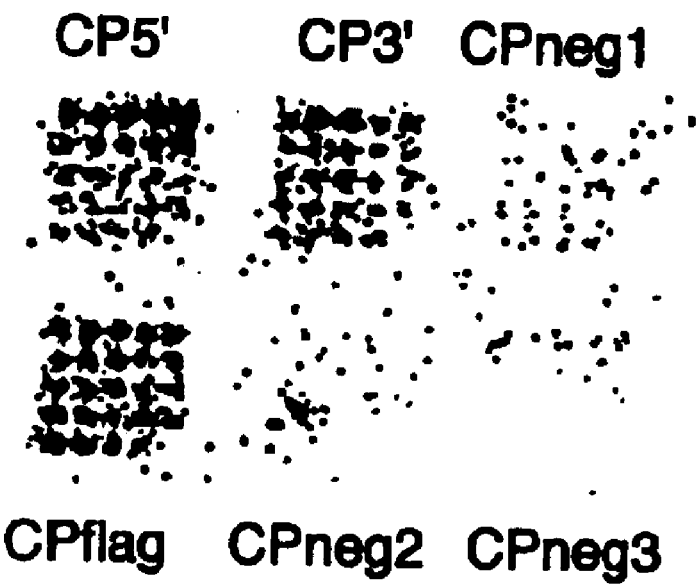
FIGS. 16 and 17 are the phosphorimage and fluorescence scan, respectively, of a $^{10}$Fn3 array, illustrating TNF-α binding.
Figure 17:
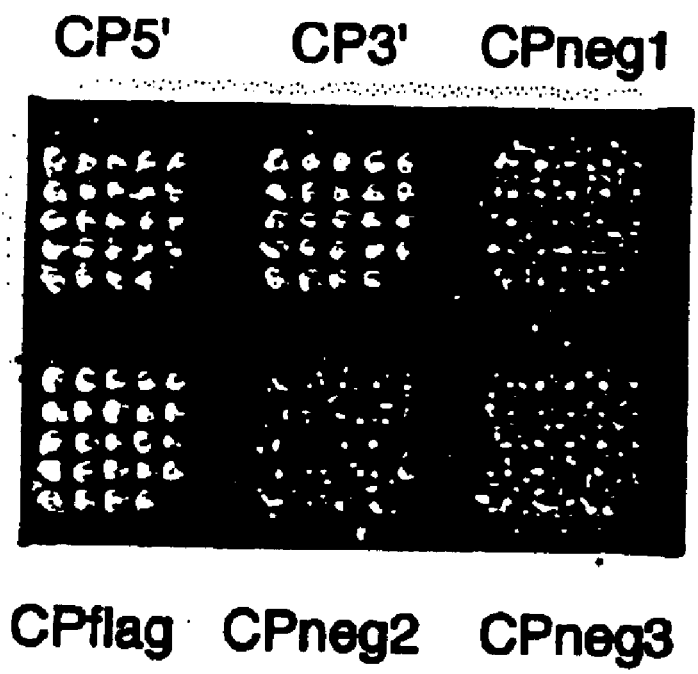

FIGS. 16 and 17 are the phosphorimage and fluorescence scan, respectively, of the same array. The phosphorimage shows where the $^{10}$Fn3 fusion hybridized based on the $^{35}$S methionine signal. The fluorescence scan shows where the labeled TNF-α bound.

Other Embodiments

Other embodiments are within the claims.

All publications, patents, and patent applications mentioned herein are hereby incorporated by reference.

What is claimed is:

1. A method for obtaining a scaffold-based protein that binds to a compound, said method comprising:
   (a) contacting a compound with a library of scaffold-based proteins under conditions that allow binding to form a compound-scaffold-based protein complex, wherein the scaffold is derived from the tenth module of human fibronectin type III ($^{10}$Fn3), said tenth module having the amino acid sequence, VSDVPRDLEVVAATPTSLLISWDAPAVTVRYYRITYGETGGNSPVQEFTVPGSKSTATISGLKPGVDYTITVYAVTGRGDSPASSKPISINYRT, said library comprising scaffold-based proteins having at least three randomized loops and being characterized by their ability to bind to a compound that is not bound by said human $^{10}$Fn3; and
   (b) obtaining, from said complex, a scaffold-based protein that binds to said compound and that has at least one amino acid alteration in each of three loops relative to the human $^{10}$Fn3 sequence.

2. A method for obtaining a compound that binds to a scaffold-based protein, said method comprising:
   (a) contacting a scaffold-based protein with a candidate compound under conditions that allow binding to form a compound-scaffold-based protein complex, wherein the scaffold is derived from the tenth module of human fibronectin type III ($^{10}$Fn3), said tenth module having the amino acid sequence, VSDVPRDLEVVAATPTSLLISWDAPAVTVRYYRITYGETGGNSPVQEFTVPGSKSTATISGLKPGVDYTITVYAVTGRGDSPASSKPISINYRT, said scaffold-based protein having at least one amino acid alteration in each of three loops relative to the human $^{10}$Fn3 sequence, said scaffold-based protein being characterized by its ability to bind to a compound that is not bound by said human $^{10}$Fn3; and (b) obtaining, from said complex, a compound that binds to said scaffold-based protein.

3. The method of claim 1, said method further comprising further randomizing at least one loop of said human fibronectin type III domain of said protein obtained in step (b) and repeating said steps (a) and (b) using said further randomized protein.

4. The method of claim 2, said method further comprising modifying said compound obtained in step (b) and repeating said steps (a) and (b) using said further modified compound.

5. The method of claim 1 or 2, wherein said compound is a protein.

6. The method of claim 1 or 2, wherein at least one of said randomized loops is extended in length relative to the corresponding loop of human $^{10}$Fn3.

7. The method of claim 1 or 2, wherein said $^{10}$Fn3 lacks an integrin-binding motif.

8. The method of claim 1 or 2, wherein said protein is covalently bound to a nucleic acid.

9. The method of claim 8, wherein said nucleic acid encodes said protein.

10. The method of claim 8, wherein said nucleic acid is RNA.

11. The method of claim 1, wherein said compound is immobilized on a solid support.

12. The method of claim 2, wherein said scaffold-based protein is immobilized on a solid support.

13. The method of claim 11 or 12, wherein said solid support is a column or microchip.

14. A method for detecting a compound in a sample, said method comprising:

(a) contacting said sample with a scaffold-based protein which binds to said compound under conditions that allow binding to form a compound-scaffold-based protein complex, wherein the scaffold is derived from the tenth module of human fibronectin type III ($^{10}$Fn3), said tenth module having the amino acid sequence, VSDVPRDLEVVAATPTSLLISWDAPAVTVRYYR ITYGETGGNSPVQEFTVPGSKSTATISGLKPGV DYTITVYAVTGRGDSPASSKPISINYRT, said scaffold-based protein having at least one amino acid alteration in each of three loops relative to the human $^{10}$Fn3 sequence, said scaffold-based protein being characterized by its ability to bind to a compound that is not bound by said human $^{10}$Fn3; and (b) detecting said complex, thereby detecting said compound in said sample.

15. The method of claim 14, wherein said scaffold-based protein is immobilized on a solid support.

16. The method of claim 15, wherein said scaffold-based protein is immobilized on said solid support as part of an array.

17. The method of claim 15, wherein said solid support is a chip or bead.

18. The method of claim 14, wherein said scaffold-based protein is covalently bound to a nucleic acid.

19. The method of claim 18, wherein said nucleic acid encodes and scaffold-based protein.

20. The method of claim 19, wherein said nucleic acid is RNA.

21. The method of claim 14, wherein said compound is a protein.

22. The method of claim 14, wherein said compound is detected by radiography, fluorescence detection, mass spectroscopy, or surface plasmon resonance.

* * * * *